(12) United States Patent
Schultheis

(10) Patent No.: US 12,274,485 B2
(45) Date of Patent: *Apr. 15, 2025

(54) BALLOON ASSEMBLY FOR VALVULOPLASTY CATHETER SYSTEM

(71) Applicant: Bolt Medical, Inc., Carlsbad, CA (US)

(72) Inventor: Eric Schultheis, San Clemente, CA (US)

(73) Assignee: BOLT MEDICAL, INC., Carlsbad, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 18/142,277

(22) Filed: May 2, 2023

(65) Prior Publication Data

US 2023/0310054 A1 Oct. 5, 2023

Related U.S. Application Data

(63) Continuation of application No. 17/553,156, filed on Dec. 16, 2021, now Pat. No. 11,672,585.

(Continued)

(51) Int. Cl.
*A61B 18/26* (2006.01)
*A61B 18/04* (2006.01)
(Continued)

(52) U.S. Cl.
CPC ........ *A61B 18/042* (2013.01); *A61B 18/1492* (2013.01); *A61B 18/26* (2013.01);
(Continued)

(58) Field of Classification Search
CPC ............ A61B 17/22022; A61B 18/042; A61B 18/1492; A61B 18/26; A61B 2017/00115;
(Continued)

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 7/2017
AU 2022227829 9/2022
(Continued)

OTHER PUBLICATIONS

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

(Continued)

*Primary Examiner* — George Manuel
(74) *Attorney, Agent, or Firm* — ROEDER & BRODER LLP; James P. Broder

(57) ABSTRACT

A method for treating a treatment site (106) within or adjacent to a heart valve (108) within a body of a patient includes the steps of generating energy with an energy source (124); receiving energy from the energy source (124) with an energy guide (122A); positioning a balloon assembly (104) adjacent to the treatment site (106), the balloon assembly (104) including an outer balloon (104B) and an inner balloon (104A) that is positioned within and at least partially spaced-apart from the outer balloon (104B) to define an interstitial space (146A) therebetween that is configured to retain a balloon fluid (132); and positioning a portion of the energy guide (122A) that receives the energy from the energy source (124) within the interstitial space (146A) between the balloons (104A, 104B) so that a plasma-induced bubble (134) is formed in the balloon fluid (132) within the interstitial space (146A).

20 Claims, 3 Drawing Sheets

Related U.S. Application Data

(60) Provisional application No. 63/136,474, filed on Jan. 12, 2021.

(51) Int. Cl.
*A61B 18/14* (2006.01)
*A61B 18/00* (2006.01)

(52) U.S. Cl.
CPC .............. *A61B 2018/00255* (2013.01); *A61B 2018/00369* (2013.01); *A61B 2018/1467* (2013.01); *A61B 2018/263* (2013.01)

(58) Field of Classification Search
CPC ........... A61B 2017/00783; A61B 2017/22008; A61B 2017/22025; A61B 2017/22051; A61B 2017/22062; A61B 2017/22087; A61B 2017/22089; A61B 2018/00154; A61B 2018/00166; A61B 2018/00255; A61B 2018/00285; A61B 2018/00369; A61B 2018/1467; A61B 2018/2211; A61B 2018/2222; A61B 2018/2261; A61B 2018/2266; A61B 2018/2272; A61B 2018/263; A61B 2018/266
See application file for complete search history.

(56) References Cited

U.S. PATENT DOCUMENTS

| | | |
|---|---|---|
| 4,799,479 A | 1/1989 | Spears |
| 4,850,351 A | 7/1989 | Herman |
| 4,913,142 A | 4/1990 | Kittrell et al. |
| 4,932,954 A | 6/1990 | Wondrazek et al. |
| 4,955,895 A | 9/1990 | Sugiyama |
| 4,960,108 A | 10/1990 | Reichel et al. |
| 4,994,059 A | 2/1991 | Kosa et al. |
| 4,998,930 A | 3/1991 | Lundahl |
| 5,034,010 A | 7/1991 | Kittrell et al. |
| 5,041,121 A | 8/1991 | Wondrazek et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,109,452 A | 4/1992 | Selvin et al. |
| 5,116,227 A | 5/1992 | Levy |
| 5,126,165 A | 6/1992 | Akihama et al. |
| 5,152,768 A | 10/1992 | Bhatta |
| 5,173,049 A | 12/1992 | Levy |
| 5,176,674 A | 1/1993 | Hofmann |
| 5,181,921 A | 1/1993 | Makita et al. |
| 5,200,838 A | 4/1993 | Nudelman |
| 5,290,277 A | 3/1994 | Vercimak et al. |
| 5,324,282 A | 6/1994 | Dodick |
| 5,328,472 A | 7/1994 | Steinke et al. |
| 5,336,184 A | 8/1994 | Teirstein |
| 5,372,138 A | 12/1994 | Crowley |
| 5,387,225 A | 2/1995 | Euteneur |
| 5,400,428 A | 3/1995 | Grace |
| 5,410,797 A | 5/1995 | Steinke et al. |
| 5,422,926 A | 6/1995 | Smith |
| 5,454,809 A | 10/1995 | Janssen |
| 5,456,680 A | 10/1995 | Taylor |
| 5,474,537 A | 12/1995 | Solar |
| 5,509,917 A | 4/1996 | Cecchetti |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,661,829 A | 8/1997 | Zheng |
| 5,697,377 A | 12/1997 | Wittkamph |
| 5,718,241 A | 2/1998 | Ben-Haim et al. |
| 5,729,583 A | 3/1998 | Tang |
| 5,764,843 A | 6/1998 | Macken et al. |
| 5,772,609 A | 6/1998 | Nguyen et al. |
| 5,860,974 A | 1/1999 | Abele |
| 5,891,135 A | 4/1999 | Jackson et al. |
| 5,906,611 A | 5/1999 | Dodick et al. |
| 5,944,697 A | 8/1999 | Benett et al. |
| 6,015,404 A | 1/2000 | Altshuler |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,356,575 B1 | 3/2002 | Fukumoto |
| 6,368,318 B1 | 4/2002 | Visuri et al. |
| 6,423,055 B1 | 7/2002 | Farr |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 3/2003 | Rabiner et al. |
| 6,538,739 B1 | 3/2003 | Visuri et al. |
| 6,548,010 B1 | 4/2003 | Stivland et al. |
| 6,560,387 B1 | 5/2003 | Hehlen et al. |
| 6,607,502 B1 | 8/2003 | Maguire et al. |
| 6,631,220 B1 | 10/2003 | Liang et al. |
| 6,652,547 B2 | 11/2003 | Rabiner et al. |
| 6,666,834 B2 | 12/2003 | Restle et al. |
| 6,702,781 B1 | 3/2004 | Reifart et al. |
| 6,773,447 B2 | 8/2004 | Laguna |
| 6,824,554 B1 | 11/2004 | Jang |
| 6,849,994 B1 | 2/2005 | White et al. |
| 6,890,317 B2 | 5/2005 | Gerdts et al. |
| 6,947,785 B1 | 9/2005 | Beatty et al. |
| 6,966,890 B2 | 11/2005 | Coyle et al. |
| 6,978,168 B2 | 12/2005 | Beatty et al. |
| 6,990,370 B1 | 1/2006 | Beatty et al. |
| 7,273,470 B2 | 9/2007 | Wantink |
| 7,309,324 B2 | 12/2007 | Hayes et al. |
| 7,367,967 B2 | 5/2008 | Eidenschink |
| 7,470,240 B2 | 12/2008 | Schultheiss et al. |
| 7,539,231 B1 | 5/2009 | Honea et al. |
| 7,569,032 B2 | 8/2009 | Naimark et al. |
| 7,599,588 B2 | 10/2009 | Eberle et al. |
| 7,641,646 B2 | 1/2010 | Kennedy, II |
| 7,713,260 B2 | 5/2010 | Lessard |
| 7,758,572 B2 | 7/2010 | Weber et al. |
| 7,762,984 B2 | 7/2010 | Kumoyama et al. |
| 7,810,395 B2 | 10/2010 | Zhou |
| 7,850,685 B2 | 12/2010 | Kunis et al. |
| 7,867,178 B2 | 1/2011 | Simnacher |
| 7,909,797 B2 | 3/2011 | Kennedy, II et al. |
| 7,967,781 B2 | 6/2011 | Simpson et al. |
| 7,972,299 B2 | 7/2011 | Carter |
| 7,985,189 B1 | 7/2011 | Ogden et al. |
| 8,021,328 B2 | 9/2011 | Lee |
| 8,029,473 B2 | 10/2011 | Carter et al. |
| 8,043,256 B2 | 10/2011 | Hansen et al. |
| 8,088,121 B2 | 1/2012 | Nishide et al. |
| 8,162,859 B2 | 4/2012 | Schultheiss et al. |
| 8,166,825 B2 | 5/2012 | Zhou |
| 8,192,368 B2 | 6/2012 | Woodruff |
| 8,267,886 B2 | 9/2012 | Ewing et al. |
| 8,292,913 B2 | 10/2012 | Warnack |
| 8,328,820 B2 | 12/2012 | Diamant |
| 8,364,235 B2 | 1/2013 | Kordis et al. |
| 8,382,738 B2 | 2/2013 | Simpson et al. |
| 8,414,527 B2 | 4/2013 | Mallaby |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,734,424 B2 | 5/2014 | Watanabe et al. |
| 8,747,416 B2 | 6/2014 | Hakala et al. |
| 8,784,362 B2 | 7/2014 | Boutilette et al. |
| 8,834,510 B2 | 9/2014 | Wilson et al. |
| 8,888,788 B2 | 11/2014 | Hakala et al. |

(56) References Cited

U.S. PATENT DOCUMENTS

| | | |
|---|---|---|
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,817 B2 | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,011,511 B2 | 4/2015 | Gregorich et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,089,669 B2 | 7/2015 | Haslinger et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,289,132 B2 | 3/2016 | Ghaffari et al. |
| 9,289,224 B2 | 3/2016 | Adams et al. |
| 9,320,530 B2 | 4/2016 | Grace |
| 9,333,000 B2 | 5/2016 | Hakala et al. |
| 9,339,632 B2 | 5/2016 | Eidenschink et al. |
| 9,364,645 B2 | 6/2016 | Erikawa |
| 9,375,223 B2 | 6/2016 | Wallace |
| 9,421,025 B2 | 8/2016 | Hawkins et al. |
| 9,433,428 B2 | 9/2016 | Hakala et al. |
| 9,433,745 B2 | 9/2016 | Cully et al. |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-gal |
| 9,566,209 B2 | 2/2017 | Katragadda et al. |
| 9,579,114 B2 | 2/2017 | Mantell et al. |
| 9,585,684 B2 | 3/2017 | Nita et al. |
| 9,592,328 B2 | 3/2017 | Jeevanandam |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,737,361 B2 | 8/2017 | Magana |
| 9,764,142 B2 | 9/2017 | Imran |
| 9,782,570 B2 | 10/2017 | Hirszowicz et al. |
| 9,814,476 B2 | 11/2017 | Adams et al. |
| 9,833,348 B2 | 12/2017 | Jordan |
| 9,839,764 B2 | 12/2017 | Chouinard |
| 9,861,377 B2 | 1/2018 | Mantell et al. |
| 9,867,629 B2 | 1/2018 | Hawkins et al. |
| 9,878,135 B2 | 1/2018 | Holzapfel et al. |
| 9,894,756 B2 | 2/2018 | Weinkam et al. |
| 9,901,704 B2 | 2/2018 | Appling et al. |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,086,175 B2 | 10/2018 | Torres et al. |
| 10,124,153 B2 | 11/2018 | Feig |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,245,410 B2 | 4/2019 | Aggerholm |
| 10,357,264 B2 | 7/2019 | Kat-Kuoy |
| 10,405,923 B2 | 9/2019 | Yu et al. |
| 10,406,031 B2 | 9/2019 | Thyzel |
| 10,406,318 B2 | 9/2019 | Williams et al. |
| 10,420,569 B2 | 9/2019 | Adams |
| 10,439,791 B2 | 10/2019 | Kalhan |
| 10,441,300 B2 | 10/2019 | Hawkins |
| 10,449,339 B2 | 10/2019 | Wilson et al. |
| 10,463,430 B2 | 11/2019 | Dick |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,583,277 B2 | 3/2020 | Rundquist et al. |
| 10,589,073 B2 | 3/2020 | Mallaby |
| 10,617,850 B2 | 4/2020 | Tal et al. |
| 10,646,240 B2 | 5/2020 | Betelia et al. |
| 10,668,245 B2 | 6/2020 | Kanae |
| 10,682,178 B2 | 6/2020 | Adams et al. |
| 10,695,531 B2 | 6/2020 | Suzuki |
| 10,702,293 B2 | 7/2020 | Adams et al. |
| 10,709,462 B2 | 7/2020 | Nguyen et al. |
| 10,709,872 B2 | 7/2020 | Alvarez et al. |
| 10,758,255 B2 | 9/2020 | Adams |
| 10,797,684 B1 | 10/2020 | Benz et al. |
| 10,799,688 B2 | 10/2020 | Calhoun et al. |
| 10,842,567 B2 | 11/2020 | Grace et al. |
| 10,850,075 B2 | 12/2020 | Tarunaga |
| 10,857,329 B2 | 12/2020 | Davies |
| 10,933,225 B2 | 3/2021 | Campbell |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 10,980,987 B2 | 4/2021 | Tarunaga |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,116,939 B2 | 9/2021 | Jamous et al. |
| 11,141,131 B2 | 10/2021 | Stigall |
| 11,207,493 B2 | 12/2021 | Suzuki et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 11,253,681 B2 | 2/2022 | Williams |
| 11,484,327 B2 | 11/2022 | Anderson et al. |
| 11,633,200 B2 | 4/2023 | Anderson et al. |
| 11,779,363 B2 | 10/2023 | Vo |
| 11,826,530 B2 | 11/2023 | Suzuki |
| 11,839,391 B2 | 12/2023 | Schultheis et al. |
| 11,911,054 B2 | 2/2024 | Singla |
| 11,911,056 B2 | 2/2024 | Anderson et al. |
| 11,918,285 B2 | 3/2024 | Sun et al. |
| 11,944,331 B2 | 4/2024 | Anderson et al. |
| 2001/0016761 A1 | 8/2001 | Rudie |
| 2001/0018569 A1* | 8/2001 | Erbel .............. A61M 60/13 604/102.01 |
| 2001/0049464 A1 | 12/2001 | Ganz |
| 2001/0051784 A1 | 12/2001 | Brisken |
| 2002/0045811 A1 | 4/2002 | Kittrell et al. |
| 2002/0052621 A1 | 5/2002 | Fried et al. |
| 2002/0065512 A1 | 5/2002 | Fjield et al. |
| 2002/0082553 A1 | 6/2002 | Duchamp |
| 2002/0183620 A1 | 12/2002 | Tearney |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0125719 A1 | 7/2003 | Furnish |
| 2003/0144654 A1 | 7/2003 | Hilal |
| 2003/0176873 A1 | 9/2003 | Chernenko et al. |
| 2004/0002677 A1 | 1/2004 | Gentsler |
| 2004/0024349 A1 | 2/2004 | Flock et al. |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0210278 A1 | 10/2004 | Boll |
| 2004/0243119 A1 | 12/2004 | Lane et al. |

(56) References Cited

U.S. PATENT DOCUMENTS

| | | |
|---|---|---|
| 2004/0249401 A1 | 12/2004 | Rabiner |
| 2004/0254570 A1 | 12/2004 | Hadsjicostis |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0259319 A1 | 11/2005 | Brooker |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0098921 A1 | 5/2006 | Benaron et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0027524 A1 | 2/2007 | Johnson |
| 2007/0043340 A1 | 2/2007 | Thyzel |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0142821 A1 | 6/2007 | Hennessy et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0280311 A1 | 12/2007 | Hofmann |
| 2007/0299392 A1 | 12/2007 | Beyar et al. |
| 2008/0033519 A1 | 2/2008 | Burwell |
| 2008/0081950 A1 | 4/2008 | Koenig et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0175539 A1 | 7/2008 | Brown |
| 2008/0195088 A1 | 8/2008 | Farr et al. |
| 2008/0214891 A1 | 9/2008 | Slenker et al. |
| 2008/0221550 A1 | 9/2008 | Lee |
| 2008/0281157 A1 | 11/2008 | Miyagi et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0131921 A1 | 5/2009 | Kurtz et al. |
| 2009/0192495 A1 | 7/2009 | Ostrovsky et al. |
| 2009/0240242 A1 | 9/2009 | Neuberger |
| 2009/0247945 A1 | 10/2009 | Levit |
| 2009/0281531 A1 | 11/2009 | Rizoiu |
| 2009/0292296 A1 | 11/2009 | Pansky |
| 2009/0296751 A1 | 12/2009 | Kewitsch et al. |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0063491 A1 | 3/2010 | Verhagen |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160838 A1 | 6/2010 | Krespi |
| 2010/0160903 A1 | 6/2010 | Krespi |
| 2010/0168572 A1 | 7/2010 | Sliwa |
| 2010/0168836 A1 | 7/2010 | Kassab |
| 2010/0168862 A1 | 7/2010 | Edie et al. |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2010/0265733 A1 | 10/2010 | O'Leary |
| 2010/0316333 A1 | 12/2010 | Luther |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0110003 A1 | 5/2013 | Surti |
| 2013/0116714 A1 | 5/2013 | Adams et al. |
| 2013/0165764 A1 | 6/2013 | Scheuermann |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |

(56) References Cited

U.S. PATENT DOCUMENTS

| | | |
|---|---|---|
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk |
| 2014/0336637 A1 | 11/2014 | Agrawal |
| 2014/0357997 A1 | 12/2014 | Hartmann |
| 2015/0003900 A1 | 1/2015 | Ullrich et al. |
| 2015/0005576 A1 | 1/2015 | Diodone et al. |
| 2015/0039002 A1 | 2/2015 | Hawkins |
| 2015/0057648 A1 | 2/2015 | Swift et al. |
| 2015/0073430 A1 | 3/2015 | Hakala et al. |
| 2015/0080875 A1 | 3/2015 | Kasprzyk et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0320432 A1 | 11/2015 | Adams |
| 2015/0342678 A1 | 12/2015 | Deladurantaye et al. |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0135891 A1 | 5/2016 | Feldman |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184526 A1 | 6/2016 | Beyar |
| 2016/0184570 A1 | 6/2016 | Grace et al. |
| 2016/0228187 A1 | 8/2016 | Gross |
| 2016/0262784 A1 | 9/2016 | Grace et al. |
| 2016/0270806 A1 | 9/2016 | Wallace |
| 2016/0302762 A1 | 10/2016 | Stigall et al. |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0192242 A1 | 7/2017 | Laycock |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 6/2018 | Kat-kuoy |
| 2018/0214677 A1 | 8/2018 | Tarunaga |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0072378 A1 | 3/2019 | Hane et al. |
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0150961 A1 | 5/2019 | Tozzi |
| 2019/0167349 A1 | 6/2019 | Shamay |
| 2019/0175111 A1 | 6/2019 | Genereux et al. |
| 2019/0175300 A1 | 6/2019 | Hom |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0321100 A1 | 10/2019 | Masotti et al. |
| 2019/0321101 A1 | 10/2019 | Massoti et al. |
| 2019/0328259 A1 | 10/2019 | Deno et al. |
| 2019/0365400 A1 | 12/2019 | Adams et al. |
| 2019/0380589 A1 | 12/2019 | Lloret |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0116302 A1 | 4/2021 | Jean-Ruel |
| 2021/0128241 A1 | 5/2021 | Schultheis |
| 2021/0137598 A1 | 5/2021 | Cook et al. |

(56) References Cited

U.S. PATENT DOCUMENTS

| | | |
|---|---|---|
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1 | 12/2021 | Fanier et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0054194 A1 | 2/2022 | Bacher et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0249166 A1 | 8/2022 | Cook et al. |
| 2022/0273324 A1 | 9/2022 | Schultheis |
| 2022/0287732 A1 | 9/2022 | Anderson et al. |
| 2022/0313293 A1 | 10/2022 | Singh |
| 2022/0313359 A1 | 10/2022 | Schultheis et al. |
| 2022/0338890 A1 | 10/2022 | Anderson et al. |
| 2022/0354578 A1 | 11/2022 | Cook |
| 2022/0387106 A1 | 12/2022 | Cook |
| 2023/0013920 A1 | 1/2023 | Massimini |
| 2023/0064371 A1 | 3/2023 | Cook et al. |
| 2023/0137107 A1 | 5/2023 | Cook et al. |
| 2023/0157754 A1 | 5/2023 | Bacher et al. |
| 2023/0200906 A1 | 6/2023 | Cook et al. |
| 2023/0233256 A1 | 7/2023 | Cook et al. |
| 2023/0240748 A1 | 8/2023 | Cook et al. |
| 2023/0248376 A1 | 8/2023 | Anderson et al. |
| 2023/0255635 A1 | 8/2023 | Schultheis et al. |
| 2023/0255688 A1 | 8/2023 | Schultheis et al. |
| 2023/0255689 A1 | 8/2023 | Schultheis et al. |
| 2023/0310054 A1 | 10/2023 | Schultheis |
| 2023/0310067 A1 | 10/2023 | Schultheis et al. |
| 2023/0310073 A1 | 10/2023 | Adams et al. |
| 2023/0338088 A1 | 10/2023 | Massimini et al. |
| 2023/0338089 A1 | 10/2023 | Schultheis |
| 2023/0414234 A1 | 12/2023 | Anderson et al. |
| 2024/0016544 A1 | 1/2024 | Schultheis et al. |
| 2024/0016545 A1 | 1/2024 | Schultheis et al. |
| 2024/0032995 A1 | 2/2024 | Schultheis et al. |
| 2024/0033002 A1 | 2/2024 | Cook |
| 2024/0041520 A1 | 2/2024 | Schultheis et al. |
| 2024/0058060 A1 | 2/2024 | Cook et al. |
| 2024/0065712 A1 | 2/2024 | Schultheis |
| 2024/0122648 A1 | 4/2024 | Cook |
| 2024/0189543 A1 | 6/2024 | Salinas |
| 2024/0216062 A1 | 7/2024 | Cook |
| 2024/0277410 A1 | 8/2024 | Cook |
| 2024/0285296 A1 | 8/2024 | Vo |
| 2024/0382258 A1 | 11/2024 | Schultheis |

FOREIGN PATENT DOCUMENTS

| | | |
|---|---|---|
| CA | 2229806 | 3/1997 |
| CA | 2281519 | 8/1998 |
| CA | 2983655 | 10/2016 |
| CA | 3209797 | 9/2022 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 113993463 | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| CN | 114053552 | 2/2022 |
| CN | 115175625 | 10/2022 |
| DE | 3038445 A1 | 5/1982 |
| DE | 3836337 A1 | 4/1990 |
| DE | 3913027 A1 | 10/1990 |
| DE | 69431758 | 1/2003 |
| DE | 10230626 | 1/2004 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 1453566 | 9/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3266487 | 1/2018 |
| EP | 3318204 | 5/2018 |
| EP | 2879607 | 2/2019 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |

(56) References Cited

FOREIGN PATENT DOCUMENTS

| | | |
|---|---|---|
| EP | 4277537 | 11/2023 |
| EP | 4297669 | 1/2024 |
| EP | 3182931 | 6/2024 |
| EP | 3950036 | 8/2024 |
| GB | 1082397 | 9/1967 |
| JP | S62275446 A | 11/1987 |
| JP | 1996089511 | 4/1996 |
| JP | H09117407 | 5/1997 |
| JP | 2004519296 | 7/2004 |
| JP | 2008506447 | 3/2008 |
| JP | 2008083273 | 4/2008 |
| JP | 2009519777 | 5/2009 |
| JP | 2009213589 | 9/2009 |
| JP | 2011524203 | 9/2011 |
| JP | 4805208 | 11/2011 |
| JP | 4808620 | 11/2011 |
| JP | 2014123147 | 7/2014 |
| JP | 2015217215 | 12/2015 |
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | WO9524867 | 9/1995 |
| WO | 1999002095 A1 | 1/1999 |
| WO | 1999020189 A1 | 4/1999 |
| WO | WO200067648 | 11/2000 |
| WO | WO2000067648 A1 | 11/2000 |
| WO | WO0103599 | 1/2001 |
| WO | WO0103599 A2 | 1/2001 |
| WO | 20060006169 A2 | 1/2006 |
| WO | WO2006006169 | 1/2006 |
| WO | WO2009121017 | 10/2009 |
| WO | WO2009149321 A1 | 12/2009 |
| WO | WO2009152352 | 12/2009 |
| WO | 2010042653 A1 | 4/2010 |
| WO | WO2011094379 | 8/2011 |
| WO | 20110126580 A2 | 10/2011 |
| WO | WO2011126580 A3 | 10/2011 |
| WO | WO2012025833 | 3/2012 |
| WO | WO2012042619 | 4/2012 |
| WO | WO20120052924 A1 | 4/2012 |
| WO | WO2012058156 | 5/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256693 | 12/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | WO2021086571 A1 | 5/2021 |
| WO | WO2021096922 A1 | 5/2021 |
| WO | WO2021101766 | 5/2021 |
| WO | WO2021101766 A1 | 5/2021 |
| WO | WO2021126762 A1 | 6/2021 |
| WO | WO2021150502 A1 | 7/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |

OTHER PUBLICATIONS

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Preisack, M., et al. "Ultrafast imaging of tissue ablation by a XeCI excimer laser in saline", Lasers in Surgery and Medicine, 1992, pp. 520-527, vol. 12, Wiley-Liss Inc.

Versluis, M., et al. "How Snapping Shrimp Snap: Through Cavitating Bubbles", Science Mag, 2000, pp. 2114-2117, vol. 289, American Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

(56) References Cited

OTHER PUBLICATIONS

Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany. Dec. 2, 2021.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421). May 2019.
Jiang et al., "Multielectrode Catheter For Substrate Mapping for Scar-related VT Ablation: A Comparison Between Grid Versus Linear Configurations." UChicago Medicine, Center for Arrhythmia Care, Chicago IL (Id 1368). Poster for conference in San Francisco, May 8-11, 2019.
Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019.

(56) References Cited

OTHER PUBLICATIONS

Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Aug. 20, 2021 in PCT Application Serial No. PCT/US2021/031130.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
International Search Report and Written Opinion dated Aug. 25, 2022 in PCT Application Serial No. PCTUS/2022/028035.
International Search Report and Written Opinion dated Sep. 15, 2022 in PCT Application Serial No. PCTUS/2022/032045.
International Search Report and Written Opinion dated Nov. 8, 2022 in PCT Application Serial No. PCTUS/2022/039678.
International Search Report and Written Opinion, PCT Application Serial No. PCT/US2022/047751 issued Feb. 10, 2023, by the European Patent Office.
International Search Report and Written Opinion, PCT Application Serial No. PCT/US2022/047691 issued Feb. 13, 2023, by the European Patent Office.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023.
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023. (Re 57PCT).
All Foreign References and Non-Patent Literature are Available in the Parent Application, U.S. Appl. No. 17/553,156. The Examiner Has Access to These Materials Through the PTO Computer Systems. If Additional Copies are Desired, Please Notify Applicants Through Their Attorneys.

Shen, Yajie et al. "High-peak-power and narrow-linewidth Q-switched Ho: YAG laser in-band pumped at 1931 nm." Applied Physics Express 13.5 (2020): 052006. (Year 2020).
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.

(56) References Cited

OTHER PUBLICATIONS

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and on Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method for Fabricating Artificial Kidney Stones of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
"Custom Medical Skived Tubing", Duke Extrusion, 2025. https://www.dukeextrusion.com/tubing-options/skived-tubing.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones for Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland. 2015.
Medlight, "Cylindircal light diffuser Model RD", Medlight S.A., Switzerland. 2015.
Mayo, Michael E., "Interaction of Laser Radiation with Urinary Calculi", Cranfield University Defense and Security, PhD Thesis, 2009, Cranfield University.

(56) References Cited

OTHER PUBLICATIONS

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies a Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for in Vitro Lithotripsy Research: a Comprehensive Review", Journal of Endourology, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing. Oct. 2015.

Zheng, W., "Optical Lenses Manufactured on Fiber Ends", IEEE, 2015, Splicer Engineering, Duncan SC USA.

Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologics, 2014, Pinnacle Biologics, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

Mohammadzadeh, M., et al. "Photoacoustic Shock Wave Emission and Cavitation from Structured Optical Fiber Tips", Applied Physics Letters, 2016, vol. 108, American Institute of Physics Publishing LLC.

Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Search Report and Written Opinion, issued by the EP/ISA, in PCT/US2021/048819, dated Jan. 14, 2022.

PathFinder Digital, "Free Space Optics vs. Fiber Optics", 2023.

International Search Report and Written Opinion, issued in Application Serial No. PCT/US2023/016152, dated Jul. 12, 2023.

\* cited by examiner

BALLOON ASSEMBLY FOR VALVULOPLASTY CATHETER SYSTEM

RELATED APPLICATIONS

This application is a continuation application of and claims priority on U.S. patent application Ser. No. 17/553,156, filed on Dec. 16, 2021, and entitled "BALLOON ASSEMBLY FOR VALVULOPLASTY CATHETER SYSTEM". Additionally, U.S. patent application Ser. No. 17/553,156 claims priority on U.S. Provisional Application Ser. No. 63/136,474, filed on Jan. 12, 2021. As far as permitted, the contents of U.S. patent application Ser. No. 17/553,156 and U.S. Provisional Application Ser. No. 63/136,474 are incorporated in their entirety herein by reference.

BACKGROUND

Vascular lesions, such as calcium deposits, within and adjacent to heart valves in the body can be associated with an increased risk for major adverse events, such as myocardial infarction, embolism, deep vein thrombosis, stroke, and the like. Severe vascular lesions, such as severely calcified vascular lesions, can be difficult to treat and achieve patency for a physician in a clinical setting.

The aortic valve is a valve of the human heart between the left ventricle and the aorta. The aortic valve functions as a one-way valve and typically includes three leaflets which open and close in unison when the valve is functioning properly. During normal operation, when the left ventricle contracts (during ventricular systole), pressure rises in the left ventricle. When the pressure in the left ventricle rises above the pressure in the aorta, the aortic valve opens, allowing blood to exit the left ventricle into the aorta. When ventricular systole ends, pressure in the left ventricle rapidly drops. When the pressure in the left ventricle decreases, the momentum of the vortex at the outlet of the valve forces the aortic valve to close. Dysfunction or improper operation of the aortic valve can result in left ventricular hypertrophy (enlargement and thickening of the walls of the left ventricle) and/or aortic valve regurgitation, which is the backflow of blood from the aorta into the left ventricle during diastole. Such issues can lead to heart failure if left uncorrected.

A calcium deposit on the aortic valve, known as aortic valve stenosis, can form adjacent to a valve wall of the aortic valve and/or on or between the leaflets of the aortic valve. Aortic valve stenosis can prevent the leaflets from opening and closing completely, which can, in turn, result in the undesired aortic valve regurgitation. Over time, such calcium deposits can cause the leaflets to become less mobile and ultimately prevent the heart from supplying enough blood to the rest of the body.

Certain methods are currently available which attempt to address aortic valve stenosis, but such methods have not been altogether satisfactory. Certain such methods include using a standard balloon valvuloplasty catheter, and artificial aortic valve replacement, which can be used to restore functionality of the aortic valve. During aortic valvuloplasty, a balloon is expanded at high pressure in the inside of the aortic valve to break apart calcification on the valve leaflets cusps and between the commissures of the valve leaflets. Usually, this procedure is done prior to placing a replacement aortic valve. Certain anatomical factors such as heavily calcified valves can prevent the valvuloplasty from being effective enough for valve placement, causing performance and safety concerns for the replacement valve. In order for the replacement valve to function correctly it must be precisely positioned over the native valve. Stated in another manner, aortic valvuloplasty often does not have enough strength to sufficiently disrupt the calcium deposit between the leaflets or at the base of the leaflets, which can subsequently adversely impact the effectiveness of any aortic valve replacement procedure. Aortic valve replacement can also be highly invasive and extremely expensive. In still another such method, a valvular stent can be placed between the leaflets to bypass the leaflets. This procedure is relatively costly, and results have found that the pressure gradient does not appreciably improve.

Thus, there is an ongoing desire to develop improved methodologies for valvuloplasty in order to more effectively and efficiently break up calcium deposits adjacent to the valve wall of the aortic valve and/or on or between the leaflets of the aortic valve. Additionally, it is desired that such improved methodologies work effectively to address not only aortic valve stenosis related to the aortic valve, but also calcification on other heart valves, such as mitral valve stenosis within the mitral valve, valvular stenosis within the tricuspid valve, and pulmonary valve stenosis within the pulmonary valve.

SUMMARY

The present invention is directed toward a method for treating a treatment site within or adjacent to a heart valve within a body of a patient. In various embodiments, the method includes the steps of generating energy with an energy source; receiving energy from the energy source with an energy guide; positioning a balloon assembly adjacent to the treatment site, the balloon assembly including an outer balloon and an inner balloon that is positioned within and at least partially spaced-apart from the outer balloon to define an interstitial space therebetween that is configured to retain a balloon fluid; and positioning a portion of the energy guide that receives the energy from the energy source within the interstitial space between the balloons so that a plasma-induced bubble is formed in the balloon fluid within the interstitial space.

In some embodiments, the method further includes the step of selectively inflating each of the balloons with the balloon fluid to expand to an inflated state so that the inner balloon is spaced apart from the outer balloon to define the interstitial space therebetween.

In certain embodiments, the step of positioning the balloon assembly includes positioning the outer balloon substantially adjacent to the treatment site when the balloons are in the inflated state.

In some embodiments, the step of selectively inflating includes the inner balloon having an inner balloon diameter, and the outer balloon having an outer balloon diameter that is greater than the inner balloon diameter of the inner balloon when the balloons are in the inflated state.

In certain embodiments, the step of selectively inflating includes the outer balloon diameter of the outer balloon being at least approximately 5% greater than the inner balloon diameter of the inner balloon when the balloons are in the inflated state.

In other embodiments, the step of selectively inflating includes the outer balloon diameter of the outer balloon being at least approximately 20% greater than the inner balloon diameter of the inner balloon when the balloons are in the inflated state.

In some embodiments, the step of selectively inflating includes the inner balloon being inflated to a greater inflation pressure than the outer balloon when the balloons are in the inflated state.

In certain embodiments, the step of selectively inflating includes the inner balloon having a first balloon shape and the outer balloon having a second balloon shape that is different from the first balloon shape when the balloons are in the inflated state.

In some embodiments, the step of positioning the balloon assembly includes the inner balloon being made from a first material, and the outer balloon being made from a second material that is different from the first material; and the step of selectively inflating includes the first material having a first compliance, and the second material having a second compliance that is greater than the first compliance so that the outer balloon expands at a faster rate than the inner balloon when the balloons are expanded to an inflated state.

In certain embodiments, the step of positioning a portion of the energy guide includes positioning the portion of the energy guide substantially directly adjacent to an outer surface of the inner balloon.

In some embodiments, the step of positioning the portion of the energy guide includes adhering the energy guide to the outer surface of the inner balloon.

In certain embodiments, the step of positioning a portion of the energy guide includes positioning the portion of the energy guide spaced apart from the outer surface of the inner balloon.

In some embodiments, the step of positioning the portion of the energy guide includes mounting a guide support structure on the outer surface of the inner balloon, and positioning the energy guide on the guide support structure so that the energy guide is positioned spaced apart from the outer surface of the inner balloon.

In certain embodiments, the heart valve includes a valve wall; and the step of positioning the balloon assembly includes positioning the balloon assembly adjacent to the valve wall.

In some embodiments, the heart valve includes a plurality of leaflets; and the step of positioning the balloon assembly includes positioning the balloon assembly adjacent to at least one of the plurality of leaflets.

In certain embodiments, the step of positioning a portion of the energy guide includes positioning a guide distal end of the energy guide within the interstitial space between the balloons approximately at a midpoint of the heart valve.

In many embodiments, the formation of the plasma-induced bubble imparts pressure waves upon the outer balloon adjacent to the treatment site.

In some embodiments, the step of generating energy includes generating pulses of energy with the energy source that are guided along the energy guide into the interstitial space between the balloons to induce the plasma-induced bubble formation in the balloon fluid within the interstitial space between the balloons.

In certain embodiments, the step of generating energy includes the energy source being a laser source that provides pulses of laser energy; and the step of receiving energy includes the energy guide including an optical fiber.

In other embodiments, the step of generating energy includes the energy source being a high voltage energy source that provides pulses of high voltage; and the step of receiving energy includes the energy guide including an electrode pair including spaced apart electrodes that extend into the interstitial space between the balloons; and wherein pulses of high voltage from the energy source are applied to the electrodes and form an electrical arc across the electrodes.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

As used herein, the terms "treatment site", "intravascular lesion" and "vascular lesion" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Additionally, other methods of delivering energy to the lesion can be utilized, including, but not limited to electric current induced plasma generation. Reference will now be made in detail to implementations of the present invention as illustrated in the accompanying drawings. The same or similar nomenclature and/or reference indicators will be used throughout the drawings and the following detailed description to refer to the same or like parts.

In the interest of clarity, not all of the routine features of the implementations described herein are shown and described. It is appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is recognized that such a development effort might be complex and time-consuming, but would nevertheless be a routine undertaking of engineering for those of ordinary skill in the art having the benefit of this disclosure.

Figure 1:
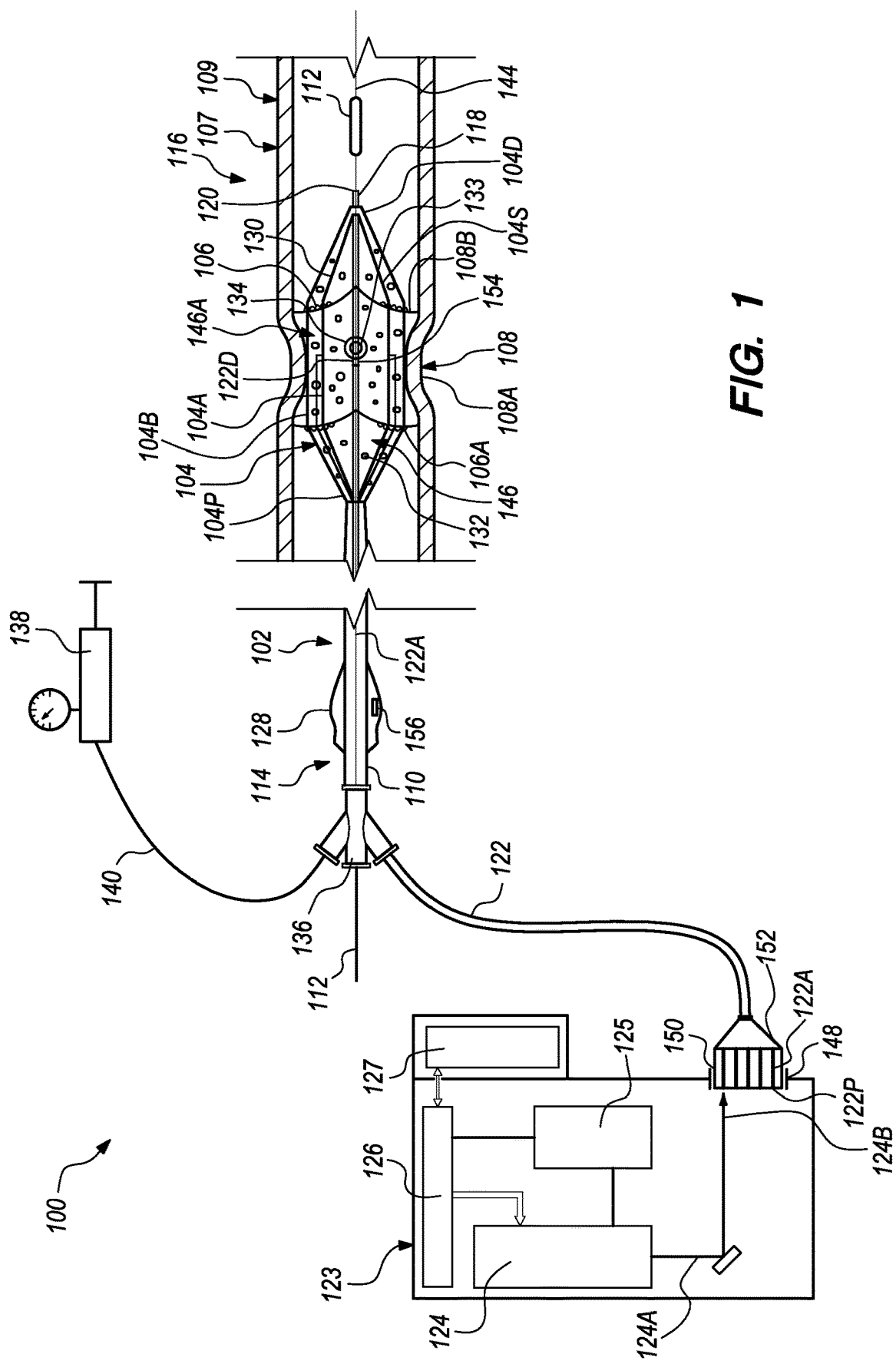
FIG. 1 is a schematic cross-sectional view of an embodiment of a catheter system in accordance with various embodiments herein, the catheter system including a valvular lithoplasty balloon assembly having features of the present invention.

The catheter systems disclosed herein can include many different forms. Referring now to FIG. 1, a schematic cross-sectional view is shown of a catheter system 100 in accordance with various embodiments. The catheter system 100 is suitable for imparting pressure waves to induce fractures in one or more treatment sites within or adjacent leaflets within the aortic valve or other appropriate heart valve. In the embodiment illustrated in FIG. 1, the catheter system 100 can include one or more of a catheter 102, an energy guide bundle 122 including one or more energy guides 122A, a source manifold 136, a fluid pump 138, a system console 123 including one or more of an energy source 124, a power source 125, a system controller 126, and a graphic user interface 127 (a "GUI"), and a handle assembly 128. Additionally, as described herein, the catheter 102 includes a valvular lithoplasty balloon assembly 104 (also sometimes referred to herein simply as a "balloon assembly"), including an inner balloon 104A and an outer balloon 104B, that is configured to be selectively positioned adjacent to a valve wall 108A (including annulus and commissures) and/or on or between adjacent leaflets 108B within a heart valve 108, e.g., the aortic valve, at a treatment site 106. Alternatively, the catheter system 100 can have more components or fewer components than those specifically illustrated and described in relation to FIG. 1.

The catheter 102 is configured to move to the treatment site 106 within or adjacent to the heart valve 108 within a body 107 of a patient 109. The treatment site 106 can include one or more vascular lesions 106A such as calcified vascular lesions, for example. Additionally, or in the alternative, the treatment site 106 can include vascular lesions 106A such as fibrous vascular lesions.

It is appreciated that the illustration of the heart valve 108 in FIG. 1, including the valve wall 108A and the leaflets 108B, is merely a simplified representation of the heart valve 108, and is not intended to represent the actual size and shape of the heart valve 108 and the components thereof. It is also appreciated that FIG. 1 further illustrates certain portions of a heart wall of a heart of the patient 109 that extend in either direction away from the heart valve 108. It is further appreciated that the heart wall of the heart is illustrated as a straight tube in FIG. 1 for purposes of simplicity, and the actual shape of the heart wall is reality is much more complex than what is actually shown in FIG. 1.

The catheter 102 can include a catheter shaft 110, a guide shaft 118, the valvular lithoplasty balloon assembly 104, and a guidewire 112.

The catheter shaft 110 can extend from a proximal portion 114 of the catheter system 100 to a distal portion 116 of the catheter system 100. The catheter shaft 110 can include a longitudinal axis 144. The guide shaft 118 can be positioned, at least in part, within the catheter shaft 110. The guide shaft 118 can define a guidewire lumen which is configured to move over the guidewire 112 and/or through which the guidewire 112 extends. The catheter shaft 110 can further include one or more inflation lumens (not shown) and/or various other lumens for various other purposes. For example, in one embodiment, the catheter shaft 110 includes a separate inflation lumen that is configured to provide a balloon fluid 132 for each of the inner balloon 104A and the outer balloon 104B of the balloon assembly 104. In some embodiments, the catheter 102 can have a distal end opening 120 and can accommodate and be tracked over the guidewire 112 as the catheter 102 is moved and positioned at or near the treatment site 106.

The balloon assembly 104 can be coupled to the catheter shaft 110. In various embodiments, the balloon assembly 104 includes the inner balloon 104A and the outer balloon 104B, which is positioned to substantially, if not entirely, encircle the inner balloon 104A. Stated in another manner, the balloon assembly 104 includes the outer balloon 104B, and the inner balloon 104A that is positioned at least substantially, if not entirely, within the outer balloon 104B. During use of the catheter system 100, the outer balloon 104B can be positioned adjacent to the valve wall 108A and/or on or between adjacent leaflets 108B within the heart valve 108 at the treatment site 106.

Each balloon 104A, 104B of the balloon assembly 104 can include a balloon proximal end 104P and a balloon distal end 104D. In some embodiments, the balloon proximal end 104P of at least one of the balloons 104A, 104B can be coupled to the catheter shaft 110. Additionally, in certain embodiments, the balloon distal end 104D of at least one of the balloons 104A, 104B can be coupled to the guide shaft 118. For example, in some embodiments, the balloon proximal end 104P of the inner balloon 104A is coupled to and/or secured to the catheter shaft 110 and the balloon distal end 104D of the inner balloon 104A is coupled to and/or secured to the guide shaft 118; and the balloon proximal end 104P of the outer balloon 104B is coupled to and/or secured to the balloon proximal end 104P of the inner balloon 104A and the balloon distal end 104D of the outer balloon 104A is coupled to and/or secured to the balloon distal end 104D of the inner balloon 104A. Alternatively, in other embodiments, the balloon proximal end 104P of each of the inner balloon 104A and the outer balloon 104B is coupled to and/or secured to the catheter shaft 110; and the balloon distal end 104D of each of the inner balloon 104A and the outer balloon 104B is coupled to and/or secured to the guide shaft 118.

It is appreciated that the inner balloon 104A can be coupled to and/or secured to the catheter shaft 110 and the guide shaft 118 in any suitable manner. For example, in one non-exclusive embodiment, the balloon proximal end 104P of the inner balloon 104A can be heat-bonded to the catheter shaft 110, and the balloon distal end 104D of the inner balloon 104A can be heat-bonded to the guide shaft 118.

Similarly, the outer balloon 104B can be coupled to and/or secured to the catheter shaft 110, the guide shaft 118 and/or the inner balloon 104A in any suitable manner. For example, in one non-exclusive embodiment, the balloon proximal end 104P of the outer balloon 104B can be heat-bonded to the catheter shaft 110, and the balloon distal end 104D of the outer balloon 1046 can be heat-bonded to the guide shaft 118. Alternatively, in another embodiment, the balloon proximal end 104P of the outer balloon 104B can be heat-bonded to the balloon proximal end 104P of the inner balloon 104A, and/or the balloon distal end 104D of the outer balloon 1046 can be heat-bonded to the balloon distal end 104D of the inner balloon 104A. Still alternatively, the inner balloon 104A can be coupled to and/or secured to the catheter shaft 110 and the guide shaft 118 in another suitable manner, and/or the outer balloon 1046 can be coupled to and/or secured to the catheter shaft 110, the guide shaft 118 and/or the inner balloon 104A in another suitable manner, such as with adhesives.

Each balloon 104A, 1046 includes a balloon wall 130 that defines a balloon interior 146. Each balloon 104A, 104B can be selectively inflated with the balloon fluid 132 to expand from a deflated state suitable for advancing the catheter 102 through a patient's vasculature, to an inflated state (as shown in FIG. 1) suitable for anchoring the catheter 102 in position relative to the treatment site 106. In particular, when the balloons 104A, 1046 are in the inflated state, the balloon wall 130 of the outer balloon 1046 is configured to be positioned substantially adjacent to the treatment site 106.

Additionally, as shown in FIG. 1, when the balloons 104A, 1046 are in the inflated state, at least a portion of the balloon wall 130 of the outer balloon 1046 is spaced apart from the balloon wall 130 of the inner balloon 104A so as to define an interstitial space 146A therebetween. It is appreciated that the interstitial space 146A between the inner balloon 104A and the outer balloon 1046 when the balloons 104A, 1046 are in the inflated state can be created in any suitable manner. For example, in certain non-exclusive embodiments, the interstitial space 146A between the inner balloon 104A and the outer balloon 104B can be created by one or more of (i) forming the inner balloon 104A and the outer balloon 1046 from different materials from one another, (ii) forming the inner balloon 104A and the outer balloon 104B to have different diameters from one another when inflated, and (iii) forming the inner balloon 104A and the outer balloon 104B to have different shapes from one another when inflated.

The balloons 104A, 104B can be formed from any suitable materials. The balloons 104A, 104B suitable for use in the balloon assembly 104 within the catheter system 100 include those that can be passed through the vasculature of a patient when in the deflated state. In various embodiments, the inner balloon 104A and the outer balloon 104B can be formed from different materials, such as having the outer balloon 104B made from a material that is more compliant than the material used for the inner balloon 104A so that when the two balloons 104A, 104B are inflated the outer balloon 104B can expand at a different, faster rate than the inner balloon 104A and therefore create a larger interstitial space 146A between the balloons 104A, 104B. More specifically, in certain embodiments, the outer balloon 104B has an outer balloon compliance over a working range as the outer balloon 104B is expanded from the deflated state to the inflated state, and the inner balloon 104A has an inner balloon compliance over a working range as the inner balloon 104A is expanded from the deflated state to the inflated state. In some such embodiments, the outer balloon compliance of the outer balloon 104B can be at least approximately 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45% or 50% greater that the inner balloon compliance of the inner balloon 104A. Alternatively, the difference between the outer balloon compliance of the outer balloon 104B and the inner balloon compliance of the inner balloon 104A can be different than the values noted above.

In some embodiments, the balloons 104A, 104B are made from silicone. In other embodiments, the balloons 104A, 104B can be made from materials such as polydimethylsiloxane (PDMS), polyurethane, polymers such as PEBAX™ material, nylon, polyethylene terephthalate (PET), or any other suitable material. Additionally, in certain embodiments, the balloons 104A, 104B can be impermeable, such that no apertures are intentionally formed into and/or through the balloon wall 130 to allow the balloon fluid 132 and/or any suitable therapeutic agent to pass therethrough.

In certain embodiments, the outer balloon 104B can be formed from compliant materials such as urethanes, lower durometer PEBAX™, and nylons, or semi-compliant materials such as PEBAX™, and nylon blends with urethanes and silicone; and the inner balloon 104A can be formed from semi-compliant materials such as PEBAX™, and nylon blends with urethanes and silicone, or non-compliant materials such as PET. More specifically, in one non-exclusive such embodiment, the outer balloon 104B can be formed from a compliant material and the inner balloon 104A can be formed from a semi-compliant material. In another non-exclusive such embodiment, the outer balloon 104B can be formed from a compliant material and the inner balloon 104A can be formed from a non-compliant material. In still another non-exclusive such embodiment, the outer balloon 104B can be formed from a semi-compliant material and the inner balloon 104A can be formed from a non-compliant material. As noted, the different compliances between the materials for the outer balloon 104B and the inner balloon 104A are configured such that the balloons 104A, 104B expand at different rates to help create the interstitial space 146A between the balloons 104A, 104B when the balloons 104A, 104B are in the inflated state.

As utilized herein, a non-compliant or semi-compliant balloon is defined as one that inflates to a predetermined shape, and changes to this shape are relatively insensitive to the internal inflation pressure. For example, in some non-exclusive applications, a non-compliant balloon is a balloon with less than approximately 6% compliance over a working range, and a semi-compliant balloon is a balloon with between approximately 6% to 12% compliance over the working range. Additionally, in such applications, a compliant balloon is a balloon with greater than 12% compliance over the working range.

The balloons 104A, 104B can have any suitable diameter (in the inflated state). In various embodiments, the balloons 104A, 104B can have a diameter (in the inflated state) ranging from less than one millimeter (mm) up to 30 mm. In some embodiments, the balloons 104A, 104B can have a diameter (in the inflated state) ranging from at least 1.5 mm up to 14 mm. In some embodiments, the balloons 104A, 104B can have a diameter (in the inflated state) ranging from at least two mm up to five mm.

In various embodiments, the outer balloon 104B and the inner balloon 104A are configured to have different diameters from one another when the balloons 104A, 104B are in the inflated state. In certain non-exclusive alternative embodiments, the inner 32%, 35%, 37%, 40%, 42%, 45%, 47% or 50% greater than the inner balloon diameter of the inner balloon 104A. Alternatively, the difference between the outer balloon diameter of the outer balloon 104B and the inner balloon diameter of the inner balloon 104A can be different than the values noted above. As noted, the difference between the outer balloon diameter and the inner balloon diameter, with the outer balloon diameter being greater than the inner balloon diameter, is configured to help create the interstitial space 146A between the balloons 104A, 104B when the balloons 104A, 104B are in the inflated state.

In some embodiments, the balloons 104A, 104B can have a length ranging from at least three mm to 300 mm. More particularly, in some embodiments, the balloons 104A, 104B can have a length ranging from at least eight mm to 200 mm. It is appreciated that balloons 104A, 104B having a relatively longer length can be positioned adjacent to larger treatment sites 106, and, thus, may be usable for imparting pressure waves onto and inducing fractures in larger vascular lesions 106A or multiple vascular lesions 106A at precise locations within the treatment site 106. It is further appreciated that longer balloons 104A, 104B can also be positioned adjacent to multiple treatment sites 106 at any one given time.

The balloons 104A, 104B can be inflated to inflation pressures of between approximately one atmosphere (atm) and 70 atm. In some embodiments, the balloons 104A, 104B can be inflated to inflation pressures of from at least 20 atm to 60 atm. In other embodiments, the balloons 104A, 104B can be inflated to inflation pressures of from at least six atm to 20 atm. In still other embodiments, the balloons 104A, 104B can be inflated to inflation pressures of from at least three atm to 20 atm. In yet other embodiments, the balloons 104A, 104B can be inflated to inflation pressures of from at least two atm to ten atm.

In certain embodiments, the inner balloon 104A and the outer balloon 104B can be inflated to different inflation pressures. In such embodiments, the inner balloon 104A can be pressurized at a higher inflation pressure than the outer balloon 104B to improve the energy transfer by better directing the energy into the vascular lesions 106A at the treatment site 106. More specifically, the improved energy transfer is achieved by keeping the balloon wall 130 of the inner balloon 104A immovable at high pressure so that the energy is not absorbed by movement of the balloon wall 130 of the inner balloon 104A, but rather is directed in a generally outward direction to the balloon wall 130 of the outer balloon 104B positioned at the treatment site 106. In certain non-exclusive embodiments, the inner balloon 104A can be inflated to an inflation pressure that is between approximately 0.1 atm and 8 atmospheres greater than the inflation pressure for the outer balloon 104B. Alternatively, the difference in inflation pressure in the inner balloon 104A and the outer balloon 104B can be different than the values noted above.

The balloons 104A, 104B can have various shapes, including, but not to be limited to, a conical shape, a square shape, a rectangular shape, a spherical shape, a conical/square shape, a conical/spherical shape, an extended spherical shape, an oval shape, a tapered shape, a bone shape, an hourglass shape, a stepped diameter shape, an offset or asymmetrical shape, or a conical offset shape. In some embodiments, the balloons 104A, 104B can include a drug eluting coating, or a drug eluting stent structure. The drug eluting coating or drug eluting stent can include one or more therapeutic agents including anti-inflammatory agents, anti-neoplastic agents, anti-angiogenic agents, and the like. In other embodiments, the balloons 104A, 104B can include any suitable type of stent structure. Additionally or in the alternative, in various applications, use of a stent is inappropriate and the valvuloplasty procedure can be followed by the positioning of an artificial replacement valve into the valve area.

In various embodiments, the shape of the inner balloon 104A can be different than the shape of the outer balloon 104B to help create the interstitial space 146A between the balloons 104A, 104B when the balloons 104A, 104B are in the inflated state. More particularly, in such embodiments, the inner balloon 104A can have a first shape and the outer balloon 104B can have a second shape that is different than the first shape to help create the interstitial space 146A and to more effectively optimize energy delivery.

The balloon fluid 132 can be a liquid or a gas. Some examples of the balloon fluid 132 suitable for use can include, but are not limited to one or more of water, saline, contrast medium, fluorocarbons, perfluorocarbons, gases, such as carbon dioxide, or any other suitable balloon fluid 132. In some embodiments, the balloon fluid 132 can be used as a base inflation fluid. In some embodiments, the balloon fluid 132 can include a mixture of saline to contrast medium in a volume ratio of approximately 50:50. In other embodiments, the balloon fluid 132 can include a mixture of saline to contrast medium in a volume ratio of approximately 25:75. In still other embodiments, the balloon fluid 132 can include a mixture of saline to contrast medium in a volume ratio of approximately 75:25. However, it is understood that any suitable ratio of saline to contrast medium can be used. The balloon fluid 132 can be tailored on the basis of composition, viscosity, and the like so that the rate of travel of the pressure waves are appropriately manipulated. In certain embodiments, the balloon fluids 132 suitable for use are biocompatible. A volume of balloon fluid 132 can be tailored by the chosen energy source 124 and the type of balloon fluid 132 used.

In some embodiments, the contrast agents used in the contrast media can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

The balloon fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the balloon fluids 132 can include those that include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system 100. By way of non-limiting examples, various lasers usable in the catheter system 100 can include neodymium:yttrium-aluminum-garnet (Nd:YAG–emission maximum=1064 nm) lasers, holmium:YAG (Ho:YAG–emission maximum=2.1 μm) lasers, or erbium:YAG (Er:YAG–emission maximum=2.94 μm) lasers. In some embodiments, the absorptive agents can be water soluble. In other embodiments, the absorptive agents are not water soluble. In some embodiments, the absorptive agents used in the balloon fluids 132 can be tailored to match the peak emission of the energy source 124. Various energy sources 124 having emission wavelengths of at least ten nanometers to one millimeter are discussed elsewhere herein.

The catheter shaft 110 of the catheter 102 can be coupled to the one or more energy guides 122A of the energy guide bundle 122 that are in optical communication with the energy source 124. Each energy guide 122A can be disposed along the catheter shaft 110 and within the interstitial space 146A between the inner balloon 104A and the outer balloon 104B. In some embodiments, each energy guide 122A can be adhered and/or attached to an outer surface 104S of the inner balloon 104A. Alternatively, in other embodiments, one or more of the energy guides 122A can be fixed onto a separate support structure (not shown in FIG. 1) such as a nitinol scaffold. In some embodiments, each energy guide 122A can be an optical fiber and the energy source 124 can be a laser. The energy source 124 can be in optical communication with the energy guides 122A at the proximal portion 114 of the catheter system 100.

In some embodiments, the catheter shaft 110 can be coupled to multiple energy guides 122A such as a first energy guide, a second energy guide, a third energy guide, a fourth energy guide, etc., which can be disposed at any suitable positions about the guide shaft 118 and/or the catheter shaft 110. For example, in certain non-exclusive embodiments, two energy guides 122A can be spaced apart by approximately 180 degrees about the circumference of the guide shaft 118 and/or the catheter shaft 110; three energy guides 122A can be spaced apart by approximately 120 degrees about the circumference of the guide shaft 118 and/or the catheter shaft 110; four energy guides 122A can be spaced apart by approximately 90 degrees about the circumference of the guide shaft 118 and/or the catheter shaft 110; five energy guides 122A can be spaced apart by approximately 72 degrees about the circumference of the guide shaft 118 and/or the catheter shaft 110; or six energy guides 122A can be spaced apart by approximately 60 degrees about the circumference of the guide shaft 118 and/or the catheter shaft 110. Still alternatively, multiple energy guides 122A need not be uniformly spaced apart from one another about the circumference of the guide shaft 118 and/or the catheter shaft 110. More particularly, it is further appreciated that the energy guides 122A can be disposed uniformly or non-uniformly about the guide shaft 118 and/or the catheter shaft 110 to achieve the desired effect in the desired locations.

The catheter system 100 and/or the energy guide bundle 122 can include any number of energy guides 122A in optical communication with the energy source 124 at the proximal portion 114, and with the balloon fluid 132 within the interstitial space 146A between the balloons 104A, 104B at the distal portion 116. For example, in some embodiments, the catheter system 100 and/or the energy guide bundle 122 can include from one energy guide 122A to greater than 30 energy guides 122A.

The energy guides 122A can have any suitable design for purposes of generating plasma-induced bubbles 134 and/or pressure waves in the balloon fluid 132 within the interstitial space 146A between the balloons 104A, 104B. Thus, the general description of the energy guides 122A as light guides is not intended to be limiting in any manner, except for as set forth in the claims appended hereto. More particularly, although the catheter systems 100 are often described with the energy source 124 as a light source and the one or more energy guides 122A as light guides, the catheter system 100 can alternatively include any suitable energy source 124 and energy guides 122A for purposes of generating the desired plasma-induced bubble(s) 134 in the balloon fluid 132 within the interstitial space 146A between the balloons 104A, 104B. For example, in one non-exclusive alternative embodiment, the energy source 124 can be configured to provide high voltage pulses, and each energy guide 122A can include an electrode pair including spaced apart electrodes that extend into the interstitial space 146A between the balloons 104A, 104B. In such embodiment, each pulse of high voltage is applied to the electrodes and forms an electrical arc across the electrodes, which, in turn, generates the plasma 134 and forms the pressure waves within the balloon fluid 132 that are utilized to provide the fracture force onto the vascular lesions 106A at the treatment site 106. Still alternatively, the energy source 124 and/or the energy guides 122A can have another suitable design and/or configuration.

In certain embodiments, the energy guides 122A can include an optical fiber or flexible light pipe. The energy guides 122A can be thin and flexible and can allow light signals to be sent with very little loss of strength. The energy guides 122A can include a core surrounded by a cladding about its circumference. In some embodiments, the core can be a cylindrical core or a partially cylindrical core. The core and cladding of the energy guides 122A can be formed from one or more materials, including but not limited to one or more types of glass, silica, or one or more polymers. The energy guides 122A may also include a protective coating, such as a polymer. It is appreciated that the index of refraction of the core will be greater than the index of refraction of the cladding.

Each energy guide 122A can guide energy along its length from a guide proximal end 122P to a guide distal end 122D having at least one optical window (not shown) that is positioned within the interstitial space 146A between the balloons 104A, 104B. In one non-exclusive embodiment, the guide distal end 122D of each energy guide 122A can be positioned within the interstitial space 146A so as to be positioned approximately at a midpoint of the heart valve 108. With such design, upon expansion of the balloons 104A, 104B to the inflated state, the pressure waves generated in the balloon fluid 132 within the interstitial space 146A between the balloons 104A, 104B can put pressure on any desired portion of the heart valve 108, e.g., the valve wall 108A, the commissures, the annulus and/or the leaflets 108B. Alternatively, the energy guides 122A can have another suitable design and/or the energy from the energy source 124 can be guided into the interstitial space 146A between the balloons 104A, 104B by another suitable method.

The energy guides 122A can assume many configurations about and/or relative to the catheter shaft 110 of the catheter 102. In some embodiments, the energy guides 122A can run parallel to the longitudinal axis 144 of the catheter shaft 110. In some embodiments, the energy guides 122A can be physically coupled to the catheter shaft 110. In other embodiments, the energy guides 122A can be disposed along a length of an outer diameter of the catheter shaft 110. In yet other embodiments, the energy guides 122A can be disposed within one or more energy guide lumens within the catheter shaft 110.

As noted, in some embodiments, each energy guide 122A can be adhered and/or attached to the outer surface 104S of the inner balloon 104A. With such design, the guide distal end 122D of each energy guide 122A can be positioned substantially directly adjacent to the outer surface 104S of the inner balloon 104A. Alternatively, in other embodiments, one or more of the energy guides 122A can be fixed onto a separate support structure such as a nitinol scaffold. With such alternative design, the guide distal end 122D of each of the energy guides 122A can be positioned spaced apart from the outer surface 104S of the inner balloon 104A.

The energy guides 122A can also be disposed at any suitable positions about the circumference of the guide shaft 118 and/or the catheter shaft 110, and the guide distal end 122D of each of the energy guides 122A can be disposed at any suitable longitudinal position relative to the length of the balloons 104A, 104B and/or relative to the length of the guide shaft 118.

In certain embodiments, the energy guides 122A can include one or more photoacoustic transducers 154, where each photoacoustic transducer 154 can be in optical communication with the energy guide 122A within which it is disposed. In some embodiments, the photoacoustic transducers 154 can be in optical communication with the guide distal end 122D of the energy guide 122A. Additionally, in such embodiments, the photoacoustic transducers 154 can have a shape that corresponds with and/or conforms to the guide distal end 122D of the energy guide 122A.

The photoacoustic transducer 154 is configured to convert light energy into an acoustic wave at or near the guide distal end 122D of the energy guide 122A. The direction of the acoustic wave can be tailored by changing an angle of the guide distal end 122D of the energy guide 122A.

In certain embodiments, the photoacoustic transducers 154 disposed at the guide distal end 122D of the energy guide 122A can assume the same shape as the guide distal end 122D of the energy guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. The energy guide 122A can further include additional photoacoustic transducers 154 disposed along one or more side surfaces of the length of the energy guide 122A.

In some embodiments, the energy guides 122A can further include one or more diverting features or "diverters" (not shown in FIG. 1) within the energy guide 122A that are configured to direct energy to exit the energy guide 122A toward a side surface which can be located at or near the guide distal end 122D of the energy guide 122A, and toward the balloon wall 130 of the outer balloon 104B. A diverting feature can include any feature of the system that diverts energy from the energy guide 122A away from its axial path toward a side surface of the energy guide 122A. Additionally, the energy guides 122A can each include one or more optical windows disposed along the longitudinal or circumferential surfaces of each energy guide 122A and in optical communication with a diverting feature. Stated in another manner, the diverting features can be configured to direct energy in the energy guide 122A toward a side surface that is at or near the guide distal end 122D, where the side surface is in optical communication with an optical window. The optical windows can include a portion of the energy guide 122A that allows energy to exit the energy guide 122A from within the energy guide 122A, such as a portion of the energy guide 122A lacking a cladding material on or about the energy guide 122A.

Examples of the diverting features suitable for use include a reflecting element, a refracting element, and a fiber diffuser. The diverting features suitable for focusing energy away from the tip of the energy guides 122A can include, but are not to be limited to, those having a convex surface, a gradient-index (GRIN) lens, and a mirror focus lens. Upon contact with the diverting feature, the energy is diverted within the energy guide 122A to one or more of a plasma generator 133 and the photoacoustic transducer 154 that is in optical communication with a side surface of the energy guide 122A. The photoacoustic transducer 154 then converts light energy into an acoustic wave that extends away from the side surface of the energy guide 122A.

The source manifold 136 can be positioned at or near the proximal portion 114 of the catheter system 100. The source manifold 136 can include one or more proximal end openings that can receive the one or more energy guides 122A of the energy guide bundle 122, the guidewire 112, and/or an inflation conduit 140 that is coupled in fluid communication with the fluid pump 138. The catheter system 100 can also include the fluid pump 138 that is configured to inflate each balloon 104A, 104B of the balloon assembly 104 with the balloon fluid 132, i.e. via the inflation conduit 140, as needed.

As noted above, in the embodiment illustrated in FIG. 1, the system console 123 includes one or more of the energy source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the energy source 124, the power source 125, the system controller 126, and the GUI 127 can be provided within the catheter system 100 without the specific need for the system console 123.

As shown, the system console 123, and the components included therewith, is operatively coupled to the catheter 102, the energy guide bundle 122, and the remainder of the catheter system 100. For example, in some embodiments, as illustrated in FIG. 1, the system console 123 can include a console connection aperture 148 (also sometimes referred to generally as a "socket") by which the energy guide bundle 122 is mechanically coupled to the system console 123. In such embodiments, the energy guide bundle 122 can include a guide coupling housing 150 (also sometimes referred to generally as a "ferrule") that houses a portion, e.g., the guide proximal end 122P, of each of the energy guides 122A. The guide coupling housing 150 is configured to fit and be selectively retained within the console connection aperture 148 to provide the mechanical coupling between the energy guide bundle 122 and the system console 123.

The energy guide bundle 122 can also include a guide bundler 152 (or "shell") that brings each of the individual energy guides 122A closer together so that the energy guides 122A and/or the energy guide bundle 122 can be in a more compact form as it extends with the catheter 102 into the heart valve 108 during use of the catheter system 100.

The energy source 124 can be selectively and/or alternatively coupled in optical communication with each of the energy guides 122A, i.e. to the guide proximal end 122P of each of the energy guides 122A, in the energy guide bundle 122. In particular, the energy source 124 is configured to generate energy in the form of a source beam 124A, such as a pulsed source beam, that can be selectively and/or alternatively directed to and received by each of the energy guides 122A in the energy guide bundle 122 as an individual guide beam 124B. Alternatively, the catheter system 100 can include more than one energy source 124. For example, in one non-exclusive alternative embodiment, the catheter system 100 can include a separate energy source 124 for each of the energy guides 122A in the energy guide bundle 122.

The energy source 124 can have any suitable design. In certain embodiments, the energy source 124 can be configured to provide sub-millisecond pulses of energy from the energy source 124 that are focused onto a small spot in order to couple it into the guide proximal end 122P of the energy guide 122A. Such pulses of energy are then directed and/or guided along the energy guides 122A to a location within the interstitial space 146A between the balloons 104A, 1046, thereby inducing the formation of plasma-induced bubble(s) (134) in the balloon fluid 132 within the interstitial space 146A between the balloons 104A, 104B, e.g., via the plasma generator 133 that can be located at or near the guide distal end 122D of the energy guide 122A. In particular, the energy emitted at the guide distal end 122D of the energy guide 122A energizes the plasma generator 133 to form the plasma-induced bubble 134 in the balloon fluid 132 within the interstitial space 146A between the balloons 104A, 104B. Formation of the plasma-induced bubble(s) 134 imparts pressure waves upon the treatment site 106. One exemplary plasma-induced bubble 134 is illustrated in FIG. 1.

In various non-exclusive alternative embodiments, the sub-millisecond pulses of energy from the energy source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of energy can be delivered to the treatment site 106 at a frequency that can be greater than 5000 Hz or less than one Hz, or any other suitable range of frequencies.

It is appreciated that although the energy source 124 is typically utilized to provide pulses of energy, the energy source 124 can still be described as providing a single source beam 124A, i.e. a single pulsed source beam.

The energy sources 124 suitable for use can include various types of light sources including lasers and lamps. Alternatively, the energy sources 124 can include any suitable type of energy source.

Suitable lasers can include short pulse lasers on the sub-millisecond timescale. In some embodiments, the energy source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to generate plasma-induced bubble(s) 134 in the balloon fluid 132 of the catheter 102. In various non-exclusive alternative embodiments, the pulse widths can include those falling within a range including from at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the energy sources 124 suitable for use in the catheter systems 100 can include those capable of producing light at wavelengths of from at least 750 nm to 2000 nm. In other embodiments, the energy sources 124 can include those capable of producing light at wavelengths of from at least 700 nm to 3000 nm. In still other embodiments, the energy sources 124 can include those capable of producing light at wavelengths of from at least 100 nm to ten micrometers (μm). Nanosecond lasers can include those having repetition rates of up to 200 kHz.

In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter system 100 can generate pressure waves having maximum pressures in the range of at least one megapascal (MPa) to 100 MPa. The maximum pressure generated by a particular catheter system 100 will depend on the energy source 124, the absorbing material, the bubble expansion, the propagation medium, the balloon material, and other factors. In various non-exclusive alternative embodiments, the catheter systems 100 can generate pressure waves having maximum pressures in the range of at least approximately two MPa to 50 MPa, at least approximately two MPa to 30 MPa, or at least approximately 15 MPa to 25 MPa.

The pressure waves can be imparted upon the treatment site 106 from a distance within a range from at least approximately 0.1 millimeters (mm) to greater than approximately 25 mm extending radially from the energy guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the energy guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide necessary power to each of the energy source 124, the system controller 126, the GUI 127, and the handle assembly 128. The power source 125 can have any suitable design for such purposes.

The system controller 126 is electrically coupled to and receives power from the power source 125. Additionally, the system controller 126 is coupled to and is configured to control operation of each of the energy source 124 and the GUI 127. The system controller 126 can include one or more processors or circuits for purposes of controlling the operation of at least the energy source 124 and the GUI 127. For example, the system controller 126 can control the energy source 124 for generating pulses of energy as desired and/or at any desired firing rate. Additionally, the system controller 126 can operate to effectively and efficiently provide the desired fracture forces adjacent to and/or on or between adjacent leaflets 1086 within the heart valve 108 at the treatment site 106.

The system controller 126 can also be configured to control operation of other components of the catheter system 100 such as the positioning of the catheter 102 and/or the balloon assembly 104 adjacent to the treatment site 106, the inflation of each balloon 104A, 104B with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100. Additionally, the GUI 127 is electrically connected to the system controller 126. With such design, the GUI 127 can be used by the user or operator to ensure that the catheter system 100 is effectively utilized to impart pressure onto and induce fractures into the vascular lesions 106A at the treatment site 106. The GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time during use of the catheter system 100. In various embodiments, the GUI 127 can include one or more colors, different sizes, varying brightness, etc., that may act as alerts to the user or operator. Additionally, or in the alternative, the GUI 127 can provide audio data or information to the user or operator. The specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. In this embodiment, the handle assembly 128 is coupled to the balloon assembly 104 and is positioned spaced apart from the balloon assembly 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the energy source 124, the fluid pump 138, and the GUI 127. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

Descriptions of various embodiments and implementations of the balloon assembly 104, and usages thereof, are described in detail herein below. However, it is further appreciated that alternative embodiments and implementations may also be employed that would be apparent to those skilled in the relevant art based on the teachings provided herein. Thus, the scope of the present embodiments and implementations is not intended to be limited to just those specifically described herein, except as recited in the claims appended hereto.

Figure 2A:
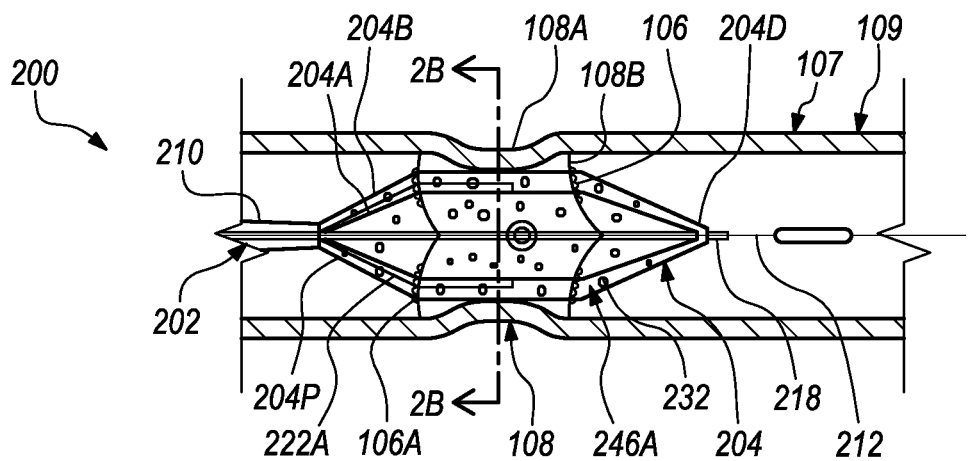
FIG. 2A is a simplified side view of a portion of a heart valve and a portion of an embodiment of the catheter system including an embodiment of the valvular lithoplasty balloon assembly.

FIG. 2A is a simplified side view of a portion of the heart valve 108, including the valve wall 108A and the leaflets 108B, and a portion of an embodiment of the catheter system 200 including an embodiment of the valvular lithoplasty balloon assembly 204. The balloon assembly 204 is again configured to be selectively positioned adjacent to the valve wall 108A and/or between adjacent leaflets 108B within the heart valve 108 at a treatment site 106 including vascular lesions 106A within the body 107 and the patient 109.

Similar to the previous embodiments, the catheter system 200 includes a catheter 202 including a catheter shaft 210, a guide shaft 218, and a guidewire 212, such as described above, and the balloon assembly 204. Additionally, the catheter system 200 will typically include various other components such as illustrated and described in relation to FIG. 1. However, such additional components are not shown in FIG. 2A for purposes of clarity.

As shown in the embodiment illustrated in FIG. 2A, the balloon assembly 204 includes an inner balloon 204A and an outer balloon 204B, which is positioned to substantially, if not entirely, encircle the inner balloon 204A. Stated in another manner, the balloon assembly 204 includes the outer balloon 204B, and the inner balloon 204A that is positioned at least substantially, if not entirely, within the outer balloon 204B. During use of the catheter system 200, the outer balloon 204B can be positioned adjacent to the valve wall 108A and/or on or between adjacent leaflets 108B within the heart valve 108 at the treatment site 106.

Each balloon 204A, 204B can include a balloon proximal end 204P and a balloon distal end 204D. As illustrated, in certain implementations, the balloon proximal end 204P of at least one of the balloons 204A, 204B can be coupled to the catheter shaft 210, and the balloon distal end 204D of at least one of the balloons 204A, 204B can be coupled to the guide shaft 218. For example, in some such implementations, the balloon proximal end 204P of the inner balloon 204A is coupled to and/or secured to the catheter shaft 210 and the balloon distal end 204D of the inner balloon 204A is coupled to and/or secured to the guide shaft 218. In such implementations, the balloon proximal end 204P of the outer balloon 204B can also be coupled to and/or secured to the catheter shaft 210, and/or the balloon proximal end 204P of the outer balloon 204B can be coupled to and/or secured to the balloon proximal end 204P of the inner balloon 204A. Additionally, in such implementations, the balloon distal end 204D of the outer balloon 204B can also be coupled to and/or secured to the guide shaft 218, and/or the balloon distal end 204D of the outer balloon 204A can be coupled to and/or secured to the balloon distal end 204D of the inner balloon 204A.

FIG. 2A further illustrates that the catheter system 200 includes one or more energy guides 222A (three are visible in FIG. 2A) that extend into the interstitial space 246A between the inner balloon 204A and the outer balloon 204B that is created when the balloons 204A, 204B are in the inflated state (as shown in FIG. 2A).

Figure 2B:
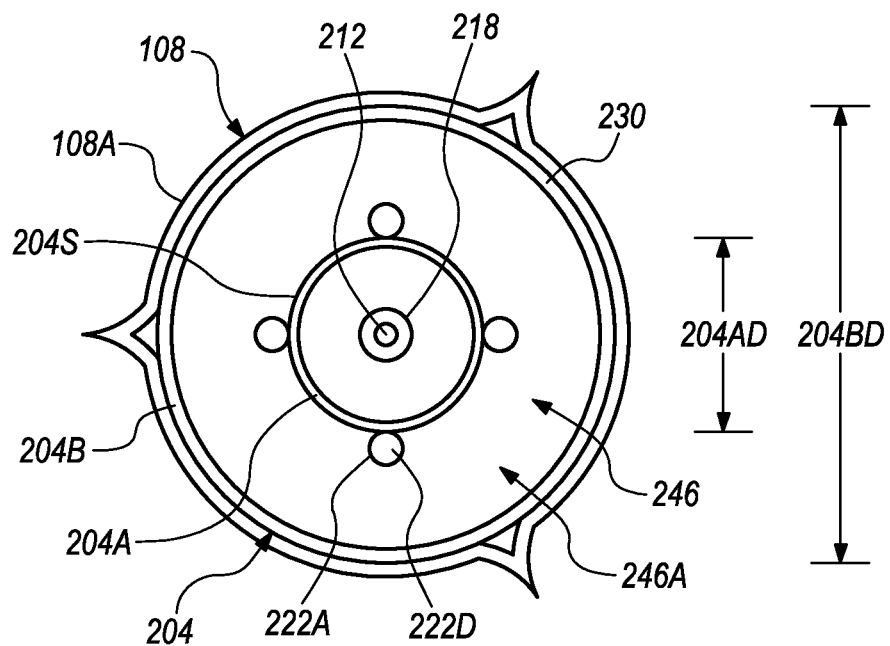
FIG. 2B is a simplified cutaway view of the catheter system including the valvular lithoplasty balloon assembly taken on line 2B-2B in FIG. 2A.

FIG. 2B is a simplified cutaway view of the heart valve 108 and the valvular lithoplasty balloon assembly 204 taken on line 2B-2B in FIG. 2A. It is appreciated that the Figures herein, including FIG. 2B, are not necessarily drawn to scale, but rather are drawn to more clearly illustrate the relative positioning of the components of the catheter system 200.

As shown, the balloon assembly 204 can be positioned within the heart valve 108, and with the outer balloon 204B of the balloon assembly 204 being positioned adjacent to the valve wall 108A and/or between adjacent leaflets 108B (illustrated in FIG. 2A) within the heart valve 108. The balloon assembly 204 is also illustrated as being positioned about the guide shaft 218, which provides the conduit through which the guidewire 212 extends, in this non-exclusive implementation.

Additionally, each balloon 204A, 204B can include a balloon wall 230 that defines a balloon interior 246, and that is configured to receive the balloon fluid 232 (illustrated in FIG. 2A) within the balloon interior 246 of each balloon 204A, 204B and/or within the interstitial space 246A between the balloons 204A, 204B. Each balloon 204A, 204B can thus be selectively inflated with the balloon fluid 232 to expand from the deflated state to the inflated state (as shown in FIG. 2B).

Also illustrated in FIG. 2B are the one or more energy guides 222A. A portion of each energy guide 222A, i.e. the guide distal end 222D, can be positioned in the balloon fluid 232 within the balloon interior 246 of the outer balloon 204B and/or within the interstitial space 246A between the balloons 204A, 204B. In this embodiment, the catheter system 200 includes four energy guides 222A, with the guide distal end 222D of each of the four energy guides 222A positioned in the balloon fluid 232 within the balloon interior 246 of the outer balloon 204B and/or within the interstitial space 246A between the balloons 204A, 204B. In one non-exclusive embodiment, the guide distal end 222D of the four energy guides 222A can be substantially uniformly spaced apart from one another by approximately 90 degrees about the inner balloon 204A. Alternatively, the catheter system 200 can include greater than four energy guides 222A or fewer than four energy guides 222A provided that the guide distal end 222D of at least one energy guide 222A is positioned within the balloon interior 246 of the outer balloon 204B and/or within the interstitial space 246A between the balloons 204A, 204B.

In this embodiment, the interstitial space 246A between the balloons 204A, 204B is created, at least in part, by a diameter of each balloon 204A, 204B being different from one another when the balloons 204A, 204B are in the inflated state. More specifically, the inner balloon 204A includes an inner balloon diameter 204AD when the inner balloon 204A is in the inflated state, and the outer balloon 204B includes an outer balloon diameter 204BD when the outer balloon 204B is in the inflated state, with the outer balloon diameter 204BD being different than, i.e. greater than, the inner balloon diameter 204AD. In certain non-exclusive alternative embodiments, the outer balloon diameter 204BD when in the inflated state can be at least approximately 1%, 2%, 3%, 5%, 7%, 10%, 12%, 15%, 17%, 20%, 22%, 25%, 27%, 30%, 32%, 35%, 37%, 40%, 42%, 45%, 47% or 50% greater than the inner balloon diameter 204AD when the inner balloon 204A is also in the inflated state. Alternatively, the difference between the outer balloon diameter 204BD of the outer balloon 204B and the inner balloon diameter 204AD of the inner balloon 204A can be different than the values noted above.

It is appreciated that in this embodiment, the balloons 204A, 204B can also have different shapes from one another and/or be formed from different materials from one another, e.g., with different compliances and/or different expansion rates, to further assist in the creation of the interstitial space 246A between the balloons 204A, 204B.

The energy guides 222A are configured to guide energy from the energy source 124 (illustrated in FIG. 1) to induce formation of plasma-induced bubble(s) 134 (illustrated in FIG. 1) in the balloon fluid 232 within the balloon interior 246 of the outer balloon 204B and/or within the interstitial space 246A between the balloons 204A, 204B, e.g., via a plasma generator 133 (illustrated in FIG. 1) located at or near the guide distal end 222D of the respective energy guide 222A. The formation of plasma-induced bubble(s) 134 imparts pressure waves and/or fracture forces upon the treatment site 106 (illustrated in FIG. 2A). Such pressure waves and/or fracture forces are utilized to break apart the vascular lesions 106A (illustrated in FIG. 2A) at specific precise locations within the heart valve 108 at the treatment site 106. More particularly, by selectively positioning the balloon assembly 204 adjacent to the treatment site 106, each of the energy guides 222A can be applied to break up the calcified vascular lesions 106A in a different precise location at the treatment site 106.

It is further appreciated that in some embodiments, the inner balloon 204A and the outer balloon 204B can be inflated to different inflation pressures, i.e. with the inner balloon 204A pressurized at a higher inflation pressure than the outer balloon 204B to improve the energy transfer by better directing the energy into the vascular lesions 106A at the treatment site 106. More specifically, the improved energy transfer is achieved by keeping the balloon wall 230 of the inner balloon 204A immovable at high pressure so that the energy is not absorbed by movement of the balloon wall 230 of the inner balloon 204A, but rather is directed in a generally outward direction to the balloon wall 230 of the outer balloon 204B positioned at the treatment site 106.

It is appreciated that bubble energy transfer from the energy guide 222A and/or the plasma generator 133 to the calcified vascular lesion 106A at the treatment site 106 is further enhanced as the balloon assembly 204 is expanded by keeping the position of the energy guides 222A and/or the plasma generators 133 close to the treatment site 106 as the diameter of the heart valve 108 expands during valvuloplasty treatment.

As shown in this embodiment, the energy guides 222A can be coupled to and/or secured to an outer surface 204S of the inner balloon 204A, e.g., with the guide distal end 222D of the energy guide 222A positioned substantially directly adjacent to the outer surface 204S of the inner balloon 204A. The energy guides 222A can be coupled to and/or secured to the outer surface 204S of the inner balloon 204A in any suitable manner. For example, in one non-exclusive embodiment, the energy guides 222A can be secured to the outer surface 204S of the inner balloon 204A with an adhesive material. Alternatively, the energy guides 222A can be coupled to and/or secured to the outer surface 204S of the inner balloon 204A in another suitable manner. Still alternatively, in other embodiments, the energy guides 222A can be positioned such that the guide distal end 222D of the energy guide 222A is positioned spaced apart from the outer surface 204S of the inner balloon 204A.

Figure 3:
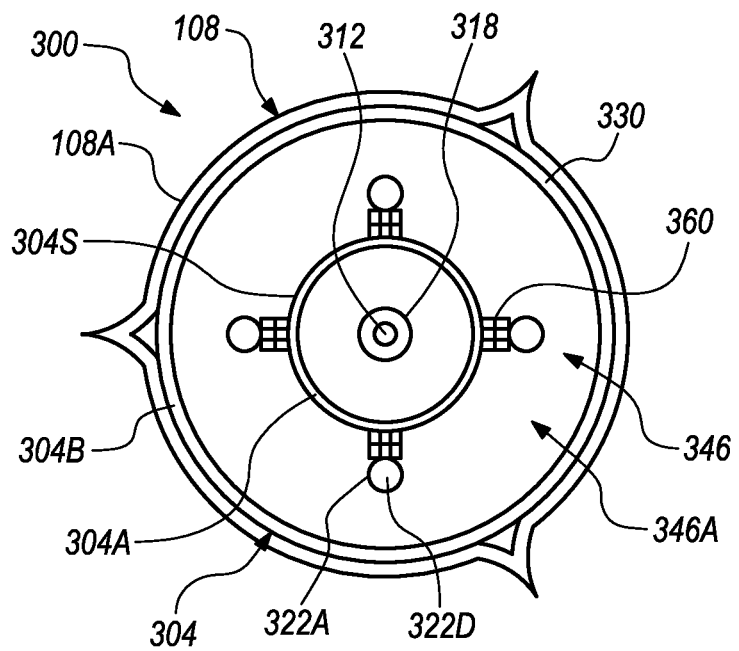
FIG. 3 is a simplified cutaway view of a portion of another embodiment of the catheter system including another embodiment of the valvular lithoplasty balloon assembly.

FIG. 3 is a simplified cutaway view of a portion of the heart valve 108, and a portion of another embodiment of the catheter system 300 including another embodiment of the valvular lithoplasty balloon assembly 304. The balloon assembly 304 is again configured to be selectively positioned adjacent to the valve wall 108A and/or between adjacent leaflets 108B (illustrated in FIG. 1) within the heart valve 108.

The balloon assembly 304 is substantially similar to what has been illustrated and described in relation to the previous embodiments. For example, in this embodiment, the balloon assembly 304 again includes an inner balloon 304A and an outer balloon 304B, which is positioned to substantially, if not entirely, encircle the inner balloon 304A. Stated in another manner, the balloon assembly 304 includes the outer balloon 304B, and the inner balloon 304A that is positioned at least substantially, if not entirely, within the outer balloon 304B. During use of the catheter system 300, the outer balloon 304B can again be positioned adjacent to the valve wall 108A and/or on or between adjacent leaflets 108B within the heart valve 108 at the treatment site 106 (illustrated in FIG. 1). The balloon assembly 304 is also illustrated as being positioned about the guide shaft 318, which provides the conduit through which the guidewire 312 extends, in this non-exclusive implementation.

Additionally, the balloons 304A, 304B of the balloon assembly 304 can again be coupled to and/or secured to the catheter shaft 110 (illustrated in FIG. 1) and the guide shaft 318 and/or to one another in a manner substantially similar to what has been described herein above.

Each balloon 304A, 304B can again include a balloon wall 330 that defines a balloon interior 346, and that is configured to receive the balloon fluid 132 (illustrated in FIG. 1) within the balloon interior 346 of each balloon 304A, 304B and/or within the interstitial space 346A between the balloons 304A, 304B. Each balloon 304A, 304B can thus be selectively inflated with the balloon fluid 132 to expand from the deflated state to the inflated state (as shown in FIG. 3).

In this embodiment, the interstitial space 346A can again be created between the balloons 304A, 304B by one or more of having the balloons 304A, 304B have different diameters than one another when in the inflated state; having the balloons 304A, 304B be of different shapes from one another when in the inflated state; and having the balloons 304A, 304B be formed from different materials from one another so that they have different compliance and/or different expansion rates as the balloons 304A, 304B are moved to the inflated state.

FIG. 3 also illustrates the one or more energy guides 322A (four energy guides 322A are shown in FIG. 3) that can be positioned at least in part within the balloon interior 346 of the outer balloon 304B and/or within the interstitial space 346A between the balloons 304A, 304B. More particularly, as shown, the guide distal end 322D of each of the energy guides 322A is shown as being positioned within the balloon interior 346 of the outer balloon 304B and/or within the interstitial space 346A between the balloons 304A, 304B. Although four energy guides 322A are specifically illustrated in FIG. 3, it is appreciated that the catheter system 300 can include any suitable number of energy guides 322A, which can also be greater than four or less than four energy guides 322A. Additionally, the energy guides 322A can have any desired spacing relative to one another about the inner balloon 304A.

Similar to the previous embodiments, the energy guides 322A are again configured to guide energy from the energy source 124 (illustrated in FIG. 1) to induce formation of plasma-induced bubble(s) 134 (illustrated in FIG. 1) in the balloon fluid 132 within the balloon interior 346 of the outer balloon 304B and/or within the interstitial space 346A between the balloons 304A, 304B, e.g., via a plasma generator 133 (illustrated in FIG. 1) located at or near the guide distal end 322D of the respective energy guide 322A. The formation of plasma-induced bubble(s) 134 imparts pressure waves and/or fracture forces upon the treatment site 106. Such pressure waves and/or fracture forces are utilized to break apart the vascular lesions 106A (illustrated in FIG. 1) at specific precise locations within the heart valve 108 at the treatment site 106. More particularly, by selectively positioning the balloon assembly 304 adjacent to the treatment site 106, each of the energy guides 322A can be applied to break up the calcified vascular lesions 106A in a different precise location at the treatment site 106.

It is further appreciated that in some embodiments, the inner balloon 304A and the outer balloon 304B can be inflated to different inflation pressures, i.e. with the inner balloon 304A pressurized at a higher inflation pressure than the outer balloon 304B to improve the energy transfer by better directing the energy into the vascular lesions 106A at the treatment site 106. More specifically, the improved energy transfer is achieved by keeping the balloon wall 330 of the inner balloon 304A immovable at high pressure so that the energy is not absorbed by movement of the balloon wall 330 of the inner balloon 304A, but rather is directed in a generally outward direction to the balloon wall 330 of the outer balloon 304B positioned at the treatment site 106. Bubble energy transfer from the energy guide 322A and/or the plasma generator 133 to the calcified vascular lesion 106A at the treatment site 106 is further enhanced as the balloon assembly 304 is expanded by keeping the position of the energy guides 322A and/or the plasma generators 133 close to the treatment site 106 as the diameter of the heart valve 108 expands during valvuloplasty treatment.

As shown in this embodiment, the energy guides 322A can be positioned spaced apart from an outer surface 304S of the inner balloon 304A, e.g., with the guide distal end 322D of the energy guide 322A positioned spaced apart from the outer surface 304S of the inner balloon 304A. The energy guides 3222A can be positioned spaced apart from the outer surface 304S of the inner balloon 304A in any suitable manner. For example, in some non-exclusive embodiments, the energy guides 322A can be secured to and/or positioned on a guide support structure 360 that is mounted on the outer surface 304S of the inner balloon 304A. In one such embodiment, the guide support structure 360 can be provided in the form of a nitinol scaffold that supports the guide distal end 322D of the respective energy guide 322A spaced apart from the outer surface 304S of the inner balloon 304A. Alternatively, the guide support structure 360 can have a different design and/or the energy guides 322A can be maintained spaced apart from the outer surface 304S of the inner balloon 304A in a different manner.

Figure 4:
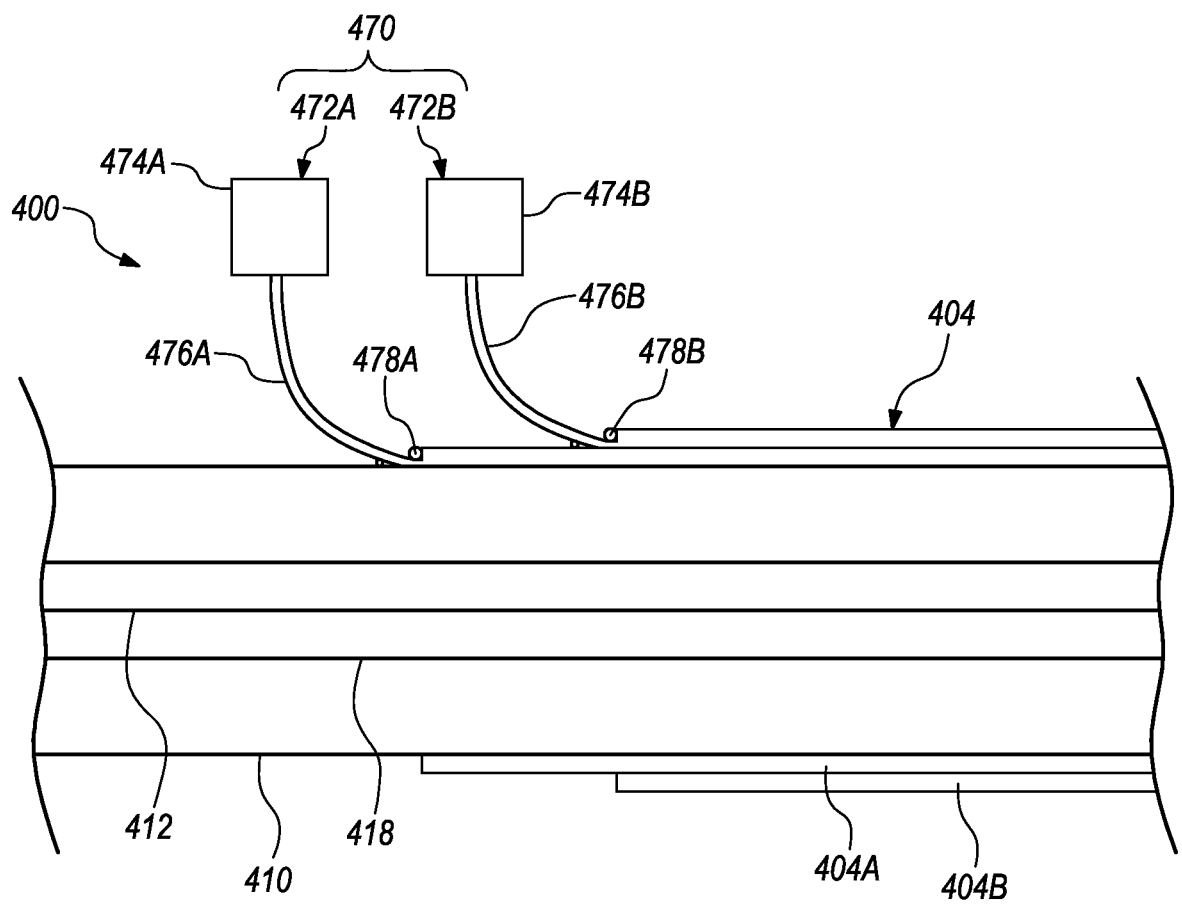
FIG. 4 is a simplified side view of a portion of a fluid flow system usable within the catheter system.

FIG. 4 is a simplified side view of a portion of a fluid flow system 470 usable within the catheter system 400. In particular, the fluid flow system 470 is configured to provide and/or direct the balloon fluid 132 (illustrated in FIG. 1) into each of the inner balloon 404A and the outer balloon 404B of the balloon assembly 404. FIG. 4 also illustrates the catheter shaft 410, the guide shaft 418 and the guidewire 412 of the catheter system 400.

The design of the fluid flow system 470 can be varied to suit the specific requirements of the catheter system 400. In certain embodiments, the fluid flow system 470 can include a first flow system 472A that is configured to provide and/or direct the balloon fluid 132 into the inner balloon 404A, and a second flow system 472B that is configured to provide and/or direct the balloon fluid 132 into the outer balloon 404B.

The design of each of the first flow system 472A and the second flow system 472B can be substantially similar to one another. More specifically, in the embodiment illustrated in FIG. 4, the first flow system 472A includes a first fluid pump 474A, a first inflation conduit 476A, and a first seal assembly 478A, and the second flow system 472B includes a second fluid pump 474B, a second inflation conduit 476B, and a second seal assembly 478B. Alternatively, the first flow system 472A and/or the second flow system 472B can include more components or fewer components than those specifically illustrated and described in relation to FIG. 4.

As shown, the first fluid pump 474A is configured to pump the balloon fluid 132 through the first fluid conduit 476A and into the balloon interior 146 (illustrated in FIG. 1) of the inner balloon 404A. The first seal assembly 478A can seal the connection of the first fluid conduit 476A into the balloon interior 146 of the inner balloon 404A. The first seal assembly 478A can have any suitable design for purposes of sealing the connection of the first fluid conduit 476A into the balloon interior 146 of the inner balloon 404A.

Similarly, the second fluid pump 474B is configured to pump the balloon fluid 132 through the second fluid conduit 476B and into the balloon interior 146 (illustrated in FIG. 1) of the outer balloon 404B. The second seal assembly 478B can seal the connection of the second fluid conduit 476B into the balloon interior 146 of the outer balloon 404B. The second seal assembly 478B can have any suitable design for purposes of sealing the connection of the second fluid conduit 476B into the balloon interior 146 of the outer balloon 404B.

In alternative embodiments, the fluid flow system 470 can be configured to include a single fluid pump that is utilized to pump the balloon fluid 132 through each of the first fluid conduit 476A and into the balloon interior 146 of the inner balloon 404A, and the second fluid conduit 476B and into the balloon interior 146 of the outer balloon 404B. More particularly, in such alternative embodiments, the single fluid pump can be provided with two pressure-regulated flow valves for each balloon 404A, 404B.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A method for treating a treatment site within or adjacent to a heart valve within a body of a patient, the method comprising the steps of:
generating energy with an energy source;
receiving energy from the energy source with an energy guide;
positioning a balloon assembly adjacent to the treatment site, the balloon assembly including an outer balloon and an inner balloon that is positioned within and at least partially spaced-apart from the outer balloon to define an interstitial space therebetween that is configured to retain a balloon fluid; and
positioning a portion of the energy guide that receives the energy from the energy source within the interstitial space between the balloons so that a plasma-induced bubble is formed in the balloon fluid within the interstitial space.

2. The method of claim 1 further comprising the step of selectively inflating each of the balloons with the balloon fluid to expand to an inflated state so that the inner balloon is spaced apart from the outer balloon to define the interstitial space therebetween.

3. The method of claim 2 wherein the step of positioning the balloon assembly includes positioning the outer balloon substantially adjacent to the treatment site when the balloons are in the inflated state.

4. The method of claim 2 wherein the step of selectively inflating includes the inner balloon having an inner balloon diameter, and the outer balloon having an outer balloon diameter that is greater than the inner balloon diameter of the inner balloon when the balloons are in the inflated state.

5. The method of claim 4 wherein the step of selectively inflating includes the outer balloon diameter of the outer balloon being at least approximately 5% greater than the inner balloon diameter of the inner balloon when the balloons are in the inflated state.

6. The method of claim 4 wherein the step of selectively inflating includes the outer balloon diameter of the outer balloon being at least approximately 20% greater than the inner balloon diameter of the inner balloon when the balloons are in the inflated state.

7. The method of claim 2 wherein the step of selectively inflating includes the inner balloon being inflated to a greater inflation pressure than the outer balloon when the balloons are in the inflated state.

8. The method of claim 2 wherein the step of selectively inflating includes the inner balloon having a first balloon shape and the outer balloon having a second balloon shape that is different from the first balloon shape when the balloons are in the inflated state.

9. The method of claim 1 wherein the step of positioning the balloon assembly includes the inner balloon being made from a first material, and the outer balloon being made from a second material that is different from the first material; and wherein the step of selectively inflating includes the first material having a first compliance, and the second material having a second compliance that is greater than the first compliance so that the outer balloon expands at a faster rate than the inner balloon when the balloons are expanded to an inflated state.

10. The method of claim 1 wherein the step of positioning a portion of the energy guide includes positioning the portion of the energy guide substantially directly adjacent to an outer surface of the inner balloon.

11. The method of claim 10 wherein the step of positioning the portion of the energy guide includes adhering the energy guide to the outer surface of the inner balloon.

12. The method of claim 1 wherein the step of positioning a portion of the energy guide includes positioning the portion of the energy guide spaced apart from the outer surface of the inner balloon.

13. The method of claim 12 the step of positioning the portion of the energy guide includes mounting a guide support structure on the outer surface of the inner balloon, and positioning the energy guide on the guide support structure so that the energy guide is positioned spaced apart from the outer surface of the inner balloon.

14. The method of claim 1 wherein the heart valve includes a valve wall; and wherein the step of positioning the balloon assembly includes positioning the balloon assembly adjacent to the valve wall.

15. The method of claim 1 wherein the heart valve includes a plurality of leaflets; and wherein the step of positioning the balloon assembly includes positioning the balloon assembly adjacent to at least one of the plurality of leaflets.

16. The method of claim 1 wherein the step of positioning a portion of the energy guide includes positioning a guide distal end of the energy guide within the interstitial space between the balloons approximately at a midpoint of the heart valve.

17. The method of claim 1 wherein the formation of the plasma-induced bubble imparts pressure waves upon the outer balloon adjacent to the treatment site.

18. The method of claim 1 wherein the step of generating energy includes generating pulses of energy with the energy source that are guided along the energy guide into the interstitial space between the balloons to induce the plasma-induced bubble formation in the balloon fluid within the interstitial space between the balloons.

19. The method of claim 1 wherein the step of generating energy includes the energy source being a laser source that provides pulses of laser energy; and wherein the step of receiving energy includes the energy guide including an optical fiber.

20. The method of claim 1 wherein the step of generating energy includes the energy source being a high voltage energy source that provides pulses of high voltage; wherein the step of receiving energy includes the energy guide including an electrode pair including spaced apart electrodes that extend into the interstitial space between the balloons; and wherein pulses of high voltage from the energy source are applied to the electrodes and form an electrical arc across the electrodes.

* * * * *